US010316068B2

(12) United States Patent
Mukhopadhyay et al.

(10) Patent No.: US 10,316,068 B2
(45) Date of Patent: Jun. 11, 2019

(54) SYNTHETIC POLYPEPTIDE HAVING A XYLOSE IMPORT ACTIVITY

(71) Applicant: The Regents of the University of California, Oakland, CA (US)

(72) Inventors: Aindrila Mukhopadhyay, Oakland, CA (US); Amanda Reider Apel, Alameda, CA (US); Mario Ouellet, Castro Valley, CA (US); Jay D. Keasling, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 15/210,834

(22) Filed: Jul. 14, 2016

(65) Prior Publication Data

US 2017/0015714 A1    Jan. 19, 2017

Related U.S. Application Data

(60) Provisional application No. 62/192,517, filed on Jul. 14, 2015.

(51) Int. Cl.
*C07K 14/395* (2006.01)
*C12N 1/18* (2006.01)

(52) U.S. Cl.
CPC ................ *C07K 14/395* (2013.01)

(58) Field of Classification Search
None
See application file for complete search history.

(56) References Cited

U.S. PATENT DOCUMENTS 7,314,974 B2 *   1/2008   Cao ............... C07K 14/195
                                                800/289

FOREIGN PATENT DOCUMENTS

WO    WO 02064766 A2 *  8/2002  ........... C07K 14/395

OTHER PUBLICATIONS

Bowie et al (Science, 1990, 257:1306-1310).*
Bork (Genome Research, 2000,10:398-400).*
Pitre, et al., "PIPE: a protein-protein interaction prediction engine based on the re-occurring short polypeptide sequences between known interacting protein pairs." BMC Bioinformatics, vol. 7:365, https://doi.org/10.1186/1471-2105-7-365 (2006).
Barnett, et al., "A history of research on yeasts 9: regulation of sugar metabolism," YEAST, vol. 22, pp. 835-894.
Snowdon, et al., "Components of the Vid30c are needed for the rapamycin-induced degradation of the high-affinity hexose transporter Hxt7p in *Saccharomyces cerevisiae*." FEMS Yeast Research, vol. 8, pp. 204-216 (2008).
Keasling, "Manufacturing Molecules Through Metabolic Engineering." SCIENCE, vol. 330, pp. 1355-1358 (2010).
Zhang, et al., "Metabolic engineering of microbial pathways for advanced biofuels production." Metabolic engineering of microbial pathways for advanced biofuels production. Current Opinion in Biotechnology, vol. 22, pp. 775-783 (2011).
Hong, et al., "Metabolic engineering of *Saccharomyces cerevisiae*: a key cell factory platform for future biorefineries" Cell Mol Life Sci vol. 69, pp. 2671-2690 (2012).
Nielsen, et al., "Metabolic engineering of yeast for production of fuels and chemicals." Current Opinion in Biotechnology, vol. 24, pp. 398-404 (2013).
Girio, et al., "Hemicelluloses for fuel ethanol: A review." Biosource Technology, vol. 101, pp. 4775-4800 (2010).
Young, et al., "Optimizing pentose utilization in yeast: the need for novel tools and approaches." Biotechnology for Biofuels, Review Open Access, vol. 3, Issue 24, pp. 1754-6834 (2010).
Kuyper, et al., "Metabolic engineering of a xylose-isomerase-expressing *Saccharomyces cerevisiae* strain for rapid anaerobic xylose fermentation." FEMS Yeast Research, vol. 5, pp. 399-409 (2005).
Kuyper, et al., "High-level functional expression of a fungal xylose isomerase: the key to efficient ethanolic fermentation of xylose by *Saccharomyces cerevisiae*?" FEMS Yeast Research, vol. 5, pp. 399-409 (2003).
Walfridsson, et al., "Ethanolic fermentation of xylose with *Saccharomyces cerevisiae* harboring the Thermus thermophilus xylA gene, which expresses an active xylose (glucose) isomerase." Applied and Environmental Microbiology, vol. 62, pp. 4648-4651 (1996).
Madhavan, et al.,"Xylose isomerase from polycentric fungus Orpinomyces: gene sequencing, cloning, and expression in *Saccharomyces cerevisiae* for bioconversion of xylose to ethanol." Applied Microbiology and Biotechnology, vol. 82, pp. 1067-1078 (2009).
Brat, et al. "Functional expression of a bacterial xylose isomerase in *Saccharomyces cerevisiae*." Applied and Environmental Microbiology, vol. 75, pp. 2304-2311 (2009).
Kotter, et al., "Isolation and characterization of the *Pichia stipitis xylitol* dehydrogenase gene, XYL2, and construction of a xylose-utilizing *Saccharomyces cerevisiae* transformant." Current Genetics, vol. 18, pp. 493-500 (1990).
Ho, et al . "Genetically engineered *Saccharomyces* yeast capable of effective cofermentation of glucose and xylose." Applied and Environmental Microbiology, vol. 64, pp. 1852-1859 (1998).
Toivari, et al., Conversion of xylose to ethanol by recombinant *Saccharomyces cerevisiae*: importance of xylulokinase (XKS1) and oxygen availability. Metabolic Engineering, vol. 3, pp. 236-249 (2001).
Lee, et al., "Effects of xylulokinase activity on ethanol production from D-xylulose by recombinant *Saccharomyces cerevisiae*." Journal of Applied Microbiology, vol. 95, pp. 847-852 (2003).
Walfridsson, et al., "Xylose-metabolizing *Saccharomyces cerevisiae* strains overexpressing the TKL1 and TAL1 genes encoding the pentose phosphate pathway enzymes transketolase and transaldolase." Applied and Environmental Microbiology, vol. 61, pp. 4184-4190 (1995).
Jin, et al, "Improvement of xylose uptake and ethanol production in recombinant *Saccharomyces cerevisiae* through an inverse metabolic engineering approach." Applied and Environmental Microbiology, vol. 71, pp. 8249-8256 (2005).

(Continued)

*Primary Examiner* — Robert A Zeman
(74) *Attorney, Agent, or Firm* — Robin C. Chiang; Lawrence Berkeley National Laboratory

(57) ABSTRACT

This disclosure provides methods and compositions related to microbial gene expression. In one aspect, a synthetic polypeptide having a xylose import activity.

5 Claims, 6 Drawing Sheets
Specification includes a Sequence Listing.

(56) References Cited

OTHER PUBLICATIONS

Wahlbom, et al., "Molecular analysis of a *Saccharomyces cerevisiae* mutant with improved ability to utilize xylose shows enhanced expression of proteins involved in transport, initial xylose metabolism, and the pentose phosphate pathway." Applied and Environmental Microbiology, vol. 69, pp. 740-746 (2003).
Latimer, et al., "Employing a combinatorial expression approach to characterize xylose utilization in *Saccharomyces cerevisiae*." Metabolic Engineering, vol. 25, pp. 20-29 (2014).
Parachin, et al., "Isolation of xylose isomerases by sequence-and function-based screening from a soil metagenomic library." Biotechnology for Biofuels, vol. 4, p. 9 (2011).
Hamacher et al., "Characterization of the xylose-transporting properties of yeast hexose transporters and their influence on xylose utilization." Microbiology (Reading, Engl) vol. 148, pp. 2783-2788 (2002).
Saloheimo, et al., "Xylose transport studies with xylose-utilizing *Saccharomyces cerevisiae* strains expressing heterologous and homologous permeases." Applied Microbiology and Biotechnology, vol. 74, pp. 1041-1052 (2007).
Gardonyi, et al., "Control of xylose consumption by xylose transport in recombinant *Saccharomyces cerevisiae*." Biotechnology Bioengineering, vol. 82, pp. 818-824 (2003).
Leandro, et al., "Hexose and pentose transport in ascomycetous yeasts: an overview." FEMS Yeast Research, vol. 9, pp. 511-525 (2009).
Wahlbom, et al., "Generation of the improved recombinant xylose-utilizing *Saccharomyces cerevisiae* TMB 3400 by random mutagenesis and physiological comparison with Pichia stipitis CBS 6054." FEMS Yeast Research, vol. 3, pp. 319-326 (2003).
Sedlak, et al., "Characterization of the effectiveness of hexose transporters for transporting xylose during glucose and xylose co-fermentation by a recombinant *Saccharomyces yeast*." Yeast, vol. 21, pp. 671-684 (2004).
Subtil, et al., "Competition between pentoses and glucose during uptake and catabolism in recombinant *Saccharomyces cerevisiae*." Biotechnology for Biofuels, vol. 5, pp. 14 (2012).
Weierstall, et al., "Cloning and characterization of three genes (SUT1-3) encoding glucose transporters of the yeast *Pichia stipitis*." Molecular Microbiology, vol. 31, pp. 871-883 (1999).
Leandro, et al., "Two glucose/xylose transporter genes from the yeast *Candida* intermedia: first molecular characterization of a yeast xylose—H+ symporter." Biochemical Journal, vol. 395, pp. 543-549 (2006).
Hector, et al., "Expression of a heterologous xylose transporter in a *Saccharomyces cerevisiae* strain engineered to utilize xylose improves aerobic xylose consumption," Applied Microbiology and Biotechnology, vol. 80, pp. 675-684 (2008).
Runquist, et al., "Comparison of heterologous xylose transporters in recombinant *Saccharomyces cerevisiae*." Biotechnology for Biofuels, vol. 3, pp. 5-7 (2010).
Du et al., "Discovery and characterization of novel d-xylose-specific transporters from Neurospora crassa and Pichia stipitis." Molecular Biosystems, vol. 6, pp. 2150-2156 (2010).
Young, et al., "Functional survey for heterologous sugar transport proteins, using *Saccharomyces cerevisiae* as a host." Applied and Environmental Microbiology, vol. 77, pp. 3311-3319.

Young, et al., "Rewiring yeast sugar transporter preference through modifying a conserved protein motif." Proceedings of the National Academy of Sciences, USA, vol. 111, pp. 131-136 (2014).
Farwick, et al., "Engineering of yeast hexose transporters to transport d-xylose without inhibition by d-glucose." Applied Biological Science, Institute of Molecular Biosciences, Goethe University Frankfurt, PNAS 1323464111 Early Edition pp. 1-6 (2014).
Viklund, et al.. "SPOCTOPUS: a combined predictor of signal peptides and membrane protein topology." Bioinformatics vol. 24, pp. 2928-2929 (2008).
Kelley, et al., "Protein structure prediction on the Web: a case study using the Phyre server." Nature Protocols, vol. 4, No. 3, pp. 363-371 (2009).
Sun, et al., "Crystal structure of a bacterial homologue of glucose transporters." GLUT1-4. Nature, vol. 490, pp. 361-366.
Ham, et al., "Design, implementation and practice of JBEI-ICE: an open source biological part registry platform and tools." Nucleic Acids Research, PMC 3467034, vol. 40, No. 18, E141, pp. 1-8 (2012).
Gietz, et al., "Transformation of yeast by lithium acetate/single-stranded carrier DNA/polyethylene glycol method." Methods in Enzymology, Vol. 350, pp. 87-96 (2002).
Fang, et al., "A vector set for systematic metabolic engineering in *Saccharomyces cerevisiae*." Yeast, vol. 28, 123-136 (2011).
Robinson, et al, "Integrative genomics viewer." Nature Biotechnology, vol. 29, pp. 24-26 (2011).
Sato, et al., "Harnessing Genetic Diversity in *Saccharomyces cerevisiae* for Fermentation of Xylose in Hydrolysates of Alkaline Hydrogen Peroxide-Pretreated Biomass." Applied and Environmental Microbiology, vol. 80, pp. 540-554 (2014).
Zha, et al., "Enhanced expression of genes involved in initial xylose metabolism and the oxidative pentose phosphate pathway in the improved xylose-utilizing *Saccharomyces cerevisiae* through evolutionary engineering." Journal of Industrial Microbiology and Biotechnology, Bioenergy/Biofuels/Biochemicals, vol. 41, pp. 27-39 (2014).
Kim, et al., "Rational and Evolutionary Engineering Approaches Uncover a Small Set of Genetic Changes Efficient for Rapid Xylose Fermentation in *Saccharomyces cerevisiae*." PLoS ONE, vol. 8, Issue 2, e57048, pp. 1-13 (2013).
Shen et al., "An efficient xylose-fermenting recombinant *Saccharomyces cerevisiae* strain obtained through adaptive evolution and its global transcription profile." Bioenergy and Biofuels Appl Microbiol Biotechnol., vol. 96, pp. 1079-1091 (2012).
Zhou, et al., "Xylose isomerase overexpression along with engineering of the pentose phosphate pathway and evolutionary engineering enable rapid xylose utilization and ethanol production by *Saccharomyces cerevisiae*." Metabolic Engineering, vol. 14, pp. 611-622 (2012).
Young, et al., "A molecular transporter engineering approach to improving xylose catabolism in *Saccharomyces cerevisiae*." Metabolic Engineering, vol. 14, pp. 401-411 (2012).
Kourmpetis, et al., "Bayesian Markov Random Field analysis for protein function prediction based on network data," PLoS ONE, vol. 5, Issue 2, e9293, pp. 1-11 (2010).
Ulitsky et al., "From E-MAPs to module maps: dissecting quantitative genetic interactions using physical interactions." Molecular Systems Biology, vol. 4, Article 209, pp. 1-12 (2008).

\* cited by examiner

US 10,316,068 B2

SYNTHETIC POLYPEPTIDE HAVING A XYLOSE IMPORT ACTIVITY

RELATED APPLICATIONS

The application claims priority to U.S. Provisional Patent Application Ser. No. 62/192,517, filed Jul. 14, 2015, which is herein incorporated by reference in its entirety.

STATEMENT OF GOVERNMENT SUPPORT

This invention was made with government support under Contract No. DE-AC02-05CH11231 awarded by the U.S. Department of Energy. The government has certain rights in this invention.

TECHNICAL FIELD

This disclosure relates generally to microbial gene expression.

BACKGROUND

In order to cost effectively produce biofuels from renewable plant biomass, all sugars, including all pentose and hexose sugars present in the raw lignocellulosic starting material, must be converted efficiently into the final products (1). The yeast, Saccharomyces cerevisiae, is an excellent host microbe for a range of industrial applications, from chemical and commodity production, to biofuel synthesis (2-4). However, S. cerevisiae does not readily uptake and use pentose sugars. This includes xylose, the most abundant pentose, and the second most abundant sugar next to glucose, found in biomass (5). While native xylose-utilizing organisms exist, they largely lack well-developed genetic tools for host engineering or exhibit low product and inhibitor tolerances. Therefore, it is important to engineer S. cerevisiae for more efficient xylose utilization, so that maximal carbon can be converted into biofuel.

Generating a yeast strain that utilizes xylose, especially in a glucose/xylose mix has been an object of extensive research for several decades (6). Great success has been achieved in boosting the native yeast utilization capability. Two approaches are now used routinely to provide for xylose utilization: overexpression of a heterologous xylose isomerase (XI) (7-11), and overexpression of the native or heterologous xylose reductase (XR) and xylitol dehydrogenase (XDH) (12, 13). Both pathways result in the transformation of xylose to xylulose, and benefit from additional overexpression of xylulokinase (XKS) to shunt the carbon into pentose-phosphate pathway (PPP) (14, 15). Further overexpression of genes encoding enzymes in the pentose-phosphate pathway, such as the transaldolase (TAL1) and the transketolase (TKL1), leads to further improvements in xylose assimilation rates (7, 16-18). Recently, it has also been shown that xylose utilization can be achieved via replacement of the native S. cerevisiae xylose utilization and PPP genes with those from the xylose-utilizing yeast Scheffersomyces stipites (19).

The improvements in intracellular xylose consumption have led to a bottleneck in xylose uptake (20). To date there has been no discovery of a sugar transporter that, in S. cerevisiae, allows for xylose uptake comparable to glucose uptake. S. cerevisiae has numerous monosaccharide transporters (HXT1-17 and GAL2), but all of them have greater specificity for hexose sugars. While a few of these (HXT1, 2, 4, 5, 7 and GAL2) can import xylose, they display rates of uptake so low that they cannot provide for growth on xylose (6, 21-25). Further, xylose uptake in these native transporters is repressed in the presence of glucose, limiting the use of these transporters in mixed sugar sources (26, 27).

Several strategies have been employed to tackle the issues with xylose transport. Much work has been devoted to bioprospecting and characterizing heterologous xylose-transporters in S. cerevisiae, resulting in the identification of several membrane proteins that can transport xylose (22, 28-33). These studies have shown that increasing xylose transport does increase utilization and final product formation, proving that xylose import is the limiting factor in utilization. However, these transporters have had limited efficacy either due to reduced growth rates, problems with substrate affinities, transport rates, or substrate inhibition.

Recently, a few studies have attempted to improve transport by engineering native transporters with encouraging results. Using a combination of bioinformatics, and mutagenesis, Young and colleagues, identified a xylose transport sequence motif, and were able to produce a mutant HXT7 strain that grew on xylose, but not glucose (34). Although this strain still showed glucose inhibition, another group was able to bypass this problem using growth to screen for glucose insensitivity (35). This approach resulted in the discovery of Gal2 and Hxt7 variants that bypass glucose inhibition. Unfortunately, the modifications that eliminated glucose repression also resulted in diminished uptake rates (Vmax). Though impressive, the resulting growth on xylose remained modest in both these studies and would benefit from further optimization.

SUMMARY

Herein is described, a synthetic polypeptide which comprises an amino acid sequence having at least 70% amino acid sequence identity to SEQ ID NO: 2, wherein said synthetic polypeptide has a xylose import activity, and the amino acid sequence of the polypeptide comprises an amino acid with a polar side chain at position 79.

Also described herein, a genetically modified microorganism which comprises a gene encoding a synthetic polypeptide comprising an amino acid sequence having at least 70% amino acid sequence identity to SEQ ID NO: 2, wherein said synthetic polypeptide has a xylose import activity, and the amino acid sequence of the polypeptide comprises an amino acid with a polar side chain at position 79.

In some embodiments, the amino acid with a polar side chain is glycine, serine, threonine, cysteine, tyrosine, asparagine, glutamine, lysine, arginine, histidine, aspartic acid, and glutamine acid.

In some embodiments, the polar side chain is a polar uncharged side chain.

In some embodiments, the genetically modified microorganism is a prokaryote. In some embodiments, the prokaryote is a bacteria.

In some embodiments, the genetically modified microorganism is a eukaryote. In some embodiments, the eukaryote is a fungus. In some embodiment, the fungus is a yeast. In some embodiments, the yeast is a Saccharomyces. In some embodiments, the Saccharomyces is Saccharomyces cerevisiae.

In some embodiments, the genetically modified microorganism imports more xylose than microorganisms without the gene encoding a synthetic polypeptide comprising an amino acid sequence having at least 70% amino acid sequence identity to SEQ ID NO: 2, wherein said synthetic polypeptide has a xylose import activity, and the amino acid sequence of the polypeptide comprises an amino acid with a polar side chain at position 79.

In some embodiments, the genetically modified microorganism in its unmodified state is unable to import xylose as a carbon source.

In some embodiments, the genetically modified microorganism has a doubling time between 4 to 100 hours.

In some embodiments, the genetically modified microorganism has a xylose transport rate between 125 to 250 nmol·min$^{-1}$·mg$^{-1}$.

In some embodiments, the genetically modified microorganism comprises one or more enzymes heterologous to the genetically modified microorganism for producing a biofuel.

Also described herein, a nucleic acid sequence encoding a synthetic polypeptide comprising an amino acid sequence having at least 70% amino acid sequence identity to SEQ ID NO: 2, wherein said synthetic polypeptide has a xylose import activity, and the amino acid sequence of the polypeptide comprises an amino acid with a polar side chain at position 79.

In some embodiments, an expression cassette comprises the nucleic acid sequence operably linked to a promoter.

Also described herein, a method for increasing xylose uptake in an microorganism which comprises introducing into an microorganism at least one heterologous expression cassette operably linked to a promoter that drives expression in the microorganism, said expression cassette comprising a nucleic acid sequence encoding a synthetic polypeptide comprises an amino acid sequence having at least 70% amino acid sequence identity to SEQ ID NO: 2, wherein said synthetic polypeptide has a xylose import activity, and the amino acid sequence of the polypeptide comprises an amino acid with a polar side chain at position 79.

Also described herein, a method for culturing microorganisms capable of using xylose as a carbon source which comprises providing a genetically modified microorganism which comprises a gene encoding a synthetic polypeptide comprising an amino acid sequence having at least 70% amino acid sequence identity to SEQ ID NO: 2, wherein said synthetic polypeptide has a xylose import activity, and the amino acid sequence of the polypeptide comprises an amino acid with a polar side chain at position 79; and culturing the genetically modified microorganism in a media.

In some embodiments, the media contains a pentose such as xylose, lyxose, ribose, ribulose, xylulose, and arabinose.

Details of one or more embodiments of the subject matter described in this specification are set forth in the accompanying drawings and the description below. Other features, aspects, and advantages will become apparent from the description, the drawings, and the claims. Note that the relative dimensions of the following figures may not be drawn to scale.

DETAILED DESCRIPTION

Figure 1A:
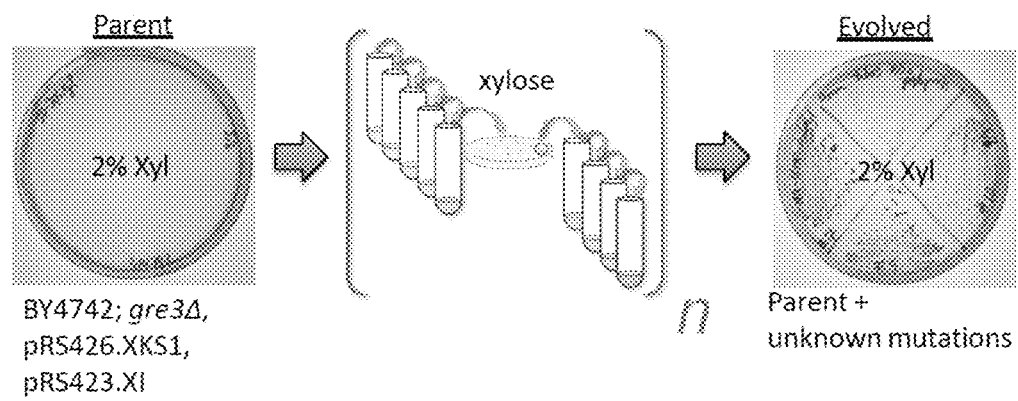
FIG. 1A shows growth of the parent strain (JBEI_ScMO001) and four representative xylose-evolved strains. Genotype of each strain listed below picture of growth.

Reference will now be made in detail to some specific examples of the invention including the best modes contemplated by the inventors for carrying out the invention. Examples of these specific embodiments are illustrated in the accompanying drawings. While the invention is described in conjunction with these specific embodiments, it will be understood that it is not intended to limit the invention to the described embodiments. On the contrary, it is intended to cover alternatives, modifications, and equivalents as may be included within the spirit and scope of the invention as defined by the appended claims.

In the following description, numerous specific details are set forth in order to provide a thorough understanding of the present invention. Particular example embodiments of the present invention may be implemented without some or all of these specific details. In other instances, well known process operations have not been described in detail in order not to unnecessarily obscure the present invention. Various techniques and mechanisms of the present invention will sometimes be described in singular form for clarity. However, it should be noted that some embodiments include multiple iterations of a technique or multiple instantiations of a mechanism unless noted otherwise.

As used herein, the term "heterologous" means not normally found in the host organism. For example, a "heterologous gene" is a gene that is not normally found in the host organism. As used herein, a "heterologous promoter" refers to a promoter that does not naturally occur adjacent a referenced gene or nucleic acid encoding a reference polypeptide, or a promoter that is not naturally operably linked to the referenced gene or nucleic acid encoding a reference polypeptide.

Herein is described, a synthetic polypeptide which comprises an amino acid sequence having at least 70% amino acid sequence identity to SEQ ID NO: 2, wherein said synthetic polypeptide has a xylose import activity, and the amino acid sequence of the polypeptide comprises an amino acid with a polar side chain at position 79. In some embodiments, the synthetic polypeptide comprises an amino acid sequence having at least 75%, 80%, 85%, 90%, 95%, or 99% amino acid sequence identity to SEQ ID NO: 2.

In some embodiments, the synthetic polypeptide comprises 1 to 12 membrane spanning domains located at the corresponding positions of the membrane spanning domains of Hxt7.

Hxt7 (GenBank Accession No. NM_001180650) is a multi-pass membrane protein involved in transmembrane transporter activity, specifically it is a high-affinity glucose transporter and more specifically a hexose transporter. Hxt7 is a member of the major facilitator superfamily and is expressed at high basal levels relative to other Hxts. Genes for Hxt6 and Hxt7 are almost identical and located in tandem 3' adjacent to Hxt3 on Chromosome IV. Hxt7's expression is repressed by high glucose levels. The topology of the Hxt7 hexose transporter follows that of a major facilitator protein that contains twelve membrane spanning domain.

The F79S mutation maps to a region that falls in the outer membrane region of a transmembrane helix. Further, while no Hxt protein is currently structurally elucidated, using the structure of a YYY protein as a scaffold suggests that the F79S mutation may directly impact the protein ligand (in this case glucose vs. xylose) binding interaction (FIG. 2).

Hxt7 Wild-Type Amino Acid Sequence

```
                                              (SEQ ID NO: 1)
MSQDAAIAEQ TPVEHLSAVD SASHSVLSTP SNKAERDEIK

AYGEGEEHEP VVEIPKRPAS AYVTVSIMCI MIAFGGFVSG

WDTGTISGFI NQTDFIRRFG MKHKDGTNYL SKVRTGLIVS

IFNIGCAIGG IILSKLGDMY GRKVGLIVVV VIYIIGIIIQ

IASINKWYQY FIGRIISGLG VGGIAVLSPM LISEVSPKHL

RGTLVSCYQL MITAGIFLGY CTNFGTKNYS NSVQWRVPLG

LCFAWALFMI GGMTFVPESP RYLAEVGKIE EAKRSIAVSN

KVAVDDPSVL AEVEAVLAGV EAEKLAGNAS WGELFSSKTK

VLQRLIMGAM IQSLQQLTGD NYFFYYGTTI FKAVGLSDSF

ETSIVLGIVN FASTFVGIYV VERYGRRTCL LWGAASMTAC

MVVYASVGVT RLWPNGQDQP SSKGAGNCMI VFACFYIFCF

ATTWAPIPYV VVSETFPLRV KSKAMSIATA ANWLWGFLIG

FFTPFITGAI NFYYGYVFMG CLVFMFFYVL LVVPETKGLT

LEEVNTMWEE GVLPWKSASW VPPSRRGANY DAEEMTHDDK

PLYKRMFSTK
```

Hxt7 F79S Amino Acid Sequence

```
                                              (SEQ ID NO: 2)
MSQDAAIAEQ TPVEHLSAVD SASHSVLSTP SNKAERDEIK

AYGEGEEHEP VVEIPKRPAS AYVTVSIMCI MIAFGGFVSG

WDTGTISGFI NQTDFIRRFG MKHKDGTNYL SKVRTGLIVS

IFNIGCAIGG IILSKLGDMY GRKVGLIVVV VIYIIGIIIQ

IASINKWYQY FIGRIISGLG VGGIAVLSPM LISEVSPKHL

RGTLVSCYQL MITAGIFLGY CTNFGTKNYS NSVQWRVPLG

LCFAWALFMI GGMTFVPESP RYLAEVGKIE EAKRSIAVSN

KVAVDDPSVL AEVEAVLAGV EAEKLAGNAS WGELFSSKTK

VLQRLIMGAM IQSLQQLTGD NYFFYYGTTI FKAVGLSDSF

ETSIVLGIVN FASTFVGIYV VERYGRRTCL LWGAASMTAC

MVVYASVGVT RLWPNGQDQP SSKGAGNCMI VFACFYIFCF

ATTWAPIPYV VVSETFPLRV KSKAMSIATA ANWLWGFLIG

FFTPFITGAI NFYYGYVFMG CLVFMFFYVL LVVPETKGLT

LEEVNTMWEE GVLPWKSASW VPPSRRGANY DAEEMTHDDK

PLYKRMFSTK
```

Hxt7 Wild-Type Coding Sequence

```
                                              (SEQ ID NO: 3)
ATGTCACAAGACGCTGCTATTGCAGAGCAAACTCCTGTGGAGCATCTCTC

TGCTGTTGACTCAGCCTCCCACTCGGTTTTATCTACACCATCAAACAAGG

CTGAAAGAGATGAAATAAAAGCTTATGGTGAAGGTGAAGAGCACGAACCT

GTCGTTGAAATTCCAAAGAGACCAGCTTCTGCCTATGTCACTGTCTCTAT

TATGTGTATCATGATCGCCTTTGGTGGTTTCGTTTTCGGTTGGGATACTG

GTACCATTTCTGGTTTCATCAATCAAACCGATTTCATCAGAAGATTTGGT

ATGAAGCATAAAGATGGTACTAATTATTTGTCTAAGGTTAGAACTGGTTT

GATTGTCTCCATTTTCAACATTGGTTGTGCCATTGGTGGTATTATTCTTT

CCAAATTGGGTGATATGTACGGTCGTAAGGTGGGTTTGATTGTCGTTGTT

GTCATCTACATCATCGGTATTATTATTCAAATTGCATCTATCAACAAATG

GTACCAATATTTCATCGGTAGAATTATTTCCGGTTTGGGTGTTGGTGGTA

TTGCCGTTTTATCTCCTATGTTGATTTCTGAAGTATCCCCAAAGCATTTA

AGGGGTACTTTAGTCTCTTGCTACCAATTGATGATTACTGCCGGTATTTT

CTTGGGTTACTGTACCAACTTCGGTACTAAGAACTACTCCAACTCTGTGC

AATGGAGAGTTCCATTAGGTTTGTGTTTTGCCTGGGCTTTGTTTATGATT

GGTGGTATGACATTTGTTCCAGAGTCTCCACGTTATTTGGCTGAAGTCGG
```

-continued

```
TAAGATCGAAGAAGCCAAACGTTCTATTGCCGTTTCTAACAAGGTTGCTG

TTGATGATCCATCTGTTTTGGCTGAAGTCGAAGCTGTCTTGGCTGGTGTA

GAGGCAGAGAAATTAGCTGGTAATGCATCCTGGGGTGAATTGTTTAGTAG

CAAGACAAAGGTCCTTCAGCGTTTGATCATGGGTGCTATGATTCAATCTC

TACAACAATTGACAGGTGATAACTATTTCTTCTACTATGGTACTACTATT

TTCAAGGCTGTTGGTTTGAGTGACTCTTTCGAAACCTCTATTGTCTTGGG

TATTGTTAACTTTGCTTCCACCTTTGTTGGTATTTACGTTGTTGAGAGAT

ATGGTCGTCGTACTTGTTTGCTATGGGTGCTGCATCCATGACTGCTTGT

ATGGTTGTCTATGCTTCCGTGGGTGTCACCAGATTATGGCCAAATGGTCA

AGACCAACCATCTTCCAAGGGTGCTGGTAACTGTATGATTGTCTTTGCCT

GTTTCTATATTTTCTGTTTTGCTACTACATGGGCTCCAATTCCTTATGTC

GTTGTTTCTGAAACTTTCCCATTGAGAGTCAAGTCTAAGGCTATGTCTAT

TGCTACAGCTGCTAATTGGTTGTGGGGTTTCTTGATTGGTTTCTTCACTC

CATTTATTACTGGTGCTATTAACTTCTACTACGGTTACGTTTTCATGGGC

TGTTTGGTCTTCATGTTCTTCTATGTTTTGTTAGTTGTTCCAGAAACTAA

GGGTTTGACTTTGGAAGAAGTCAACACCATGTGGGAAGAAGGTGTTCTAC

CATGGAAGTCTGCCTCATGGGTTCCACCATCCAGAAGAGGTGCCAACTAC

GACGCTGAAGAAATGACTCACGATGACAAGCCATTGTACAAGAGAATGTT

CAGCACCAAATAA
```

Hxt7 F79S Coding Sequence

```
                                        (SEQ ID NO: 4)
ATGTCACAAGACGCTGCTATTGCAGAGCAAACTCCTGTGGAGCATCTCTC

TGCTGTTGACTCAGCCTCCCACTCGGTTTTATCTACACCATCAAACAAGG

CTGAAAGAGATGAAATAAAAGCTTATGGTGAAGGTGAAGAGCACGAACCT

GTCGTTGAAATTCCAAAGAGACCAGCTTCTGCCTATGTCACTGTCTCTAT

TATGTGTATCATGATCGCCTTTGGTGGTTTCGTTTCCGGTTGGGATACTG

GTACCATTTCTGGTTTCATCAATCAAACCGATTTCATCAGAAGATTTGGT

ATGAAGCATAAAGATGGTACTAATTATTTGTCTAAGGTTAGAACTGGTTT

GATTGTCTCCATTTTCAACATTGGTGTGCCATTGGTGGTATTATTCTTT

CCAAATTGGGTGATATGTACGGTCGTAAGGTGGGTTTGATTGTCGTTGTT

GTCATCTACATCATCGGTATTATTATTCAAATTGCATCTATCAACAAATG

GTACCAATATTTCATCGGTAGAATTATTTCCGGTTTGGGTGTTGGTGGTA

TTGCCGTTTTATCTCCTATGTTGATTTCTGAAGTATCCCCAAAGCATTTA

AGGGGTACTTTAGTCTCTTGCTACCAATTGATGATTACTGCCGGTATTTT

CTTGGGTTACTGTACCAACTTCGGTACTAAGAACTACTCCAACTCTGTGC

AATGGAGAGTTCCATTAGGTTTGTGTTTTGCCTGGGCTTTGTTTATGATT

GGTGGTATGACATTTGTTCCAGAGTCTCCACGTTATTTGGCTGAAGTCGG

TAAGATCGAAGAAGCCAAACGTTCTATTGCCGTTTCTAACAAGGTTGCTG

TTGATGATCCATCTGTTTTGGCTGAAGTCGAAGCTGTCTTGGCTGGTGTA

GAGGCAGAGAAATTAGCTGGTAATGCATCCTGGGGTGAATTGTTTAGTAG

CAAGACAAAGGTCCTTCAGCGTTTGATCATGGGTGCTATGATTCAATCTC

TACAACAATTGACAGGTGATAACTATTTCTTCTACTATGGTACTACTATT

TTCAAGGCTGTTGGTTTGAGTGACTCTTTCGAAACCTCTATTGTCTTGGG

TATTGTTAACTTTGCTTCCACCTTTGTTGGTATTTACGTTGTTGAGAGAT

ATGGTCGTCGTACTTGTTTGCTATGGGTGCTGCATCCATGACTGCTTGT

ATGGTTGTCTATGCTTCCGTGGGTGTCACCAGATTATGGCCAAATGGTCA

AGACCAACCATCTTCCAAGGGTGCTGGTAACTGTATGATTGTCTTTGCCT

GTTTCTATATTTTCTGTTTTGCTACTACATGGGCTCCAATTCCTTATGTC

GTTGTTTCTGAAACTTTCCCATTGAGAGTCAAGTCTAAGGCTATGTCTAT

TGCTACAGCTGCTAATTGGTTGTGGGGTTTCTTGATTGGTTTCTTCACTC

CATTTATTACTGGTGCTATTAACTTCTACTACGGTTACGTTTTCATGGGC

TGTTTGGTCTTCATGTTCTTCTATGTTTTGTTAGTTGTTCCAGAAACTAA

GGGTTTGACTTTGGAAGAAGTCAACACCATGTGGGAAGAAGGTGTTCTAC

CATGGAAGTCTGCCTCATGGGTTCCACCATCCAGAAGAGGTGCCAACTAC

GACGCTGAAGAAATGACTCACGATGACAAGCCATTGTACAAGAGAATGTT

CAGCACCAAATAA
```

Also described herein, a genetically modified microorganism which comprises a gene encoding a synthetic polypeptide comprising an amino acid sequence having at least 70% amino acid sequence identity to SEQ ID NO: 2, wherein said synthetic polypeptide has a xylose import activity, and the amino acid sequence of the polypeptide comprises an amino acid with a polar side chain at position 79. In some embodiments, the amino acid a the polar side chain is glycine, serine, threonine, cysteine, tyrosine, asparagine, glutamine, lysine, arginine, histidine, aspartic acid, or glutamine acid. In some embodiments, the polar amino acid is a polar, uncharged amino acid. In some embodiments, the polar, uncharged amino acid is glycine, serine, threonine, cysteine, tyrosine, asparagine, or glutamine.

In some embodiments, the genetically modified microorganism is a fungus. In some embodiments, the fungus is a yeast. In some embodiments, the yeast is a *Saccharomyces* such as *Saccharomyces cerevisiae*. In some embodiments, the yeast is *Pichia stipitis, Pachysolen tannophilus*, and *Candida shehatae*.

In some embodiments, the genetically modified microorganism imports more xylose than microorganisms without the gene encoding a synthetic polypeptide comprising an amino acid sequence having at least 70% amino acid sequence identity to SEQ ID NO: 2, wherein said synthetic polypeptide has a xylose import activity, and the amino acid sequence of the polypeptide comprises an amino acid with a polar side chain at position 79.

In some embodiments, the genetically modified microorganism in its unmodified state is unable to import xylose as a carbon source.

In some embodiments, the genetically modified microorganism has a doubling time between 4 to 100 hours. In some embodiments, the doubling time is between 4 to 90 hours. In some embodiments, the doubling time is between 4 to 80 hours. In some embodiments, the doubling time is between 4 to 70 hours. In some embodiments, the doubling time is between 4 to 60 hours. In some embodiments, the doubling time is between 4 to 50 hours. In some embodiments, the doubling time is between 4 to 40 hours. In some embodiments, the doubling time is between 4 to 30 hours. In some embodiments, the doubling time is between 4 to 20 hours. In some embodiments, the doubling time is between 4 to 10 hours. In some embodiments, the genetically modified microorganism has a doubling time of less than 9 hours.

In some embodiments, the genetically modified microorganism has a xylose transport rate between 125 to 250 nmol·min$^{-1}$·mg$^{-1}$. In some embodiments, the xylose transport rate is between 150 to 250 nmol·min$^{-1}$·mg$^{-1}$. In some embodiments, the xylose transport rate is between 175 to 250 nmol·min$^{-1}$·mg$^{-1}$. In some embodiments, the xylose transport rate is between 200 to 250 nmol·min$^{-1}$·mg$^{-1}$. In some embodiments, the xylose transport rate is between 225 to 250 nmol·min$^{-1}$·mg$^{-1}$. In some embodiments, the genetically modified microorganism has a xylose transport rate of greater than 186.4 nmol·min$^{-1}$·mg$^{-1}$.

In some embodiments, the genetically modified microorganism comprises one or more biosynthetic pathways and/or enzymes heterologous to the genetically modified microorganism for producing a biofuel, valuable chemical, compound of interest, or a precursor thereof. Suitable biosynthetic pathways and/or enzymes, and nucleic acids encoding thereof, for use in the present invention are disclosed in U.S. Pat. Nos. 7,670,825; 7,736,882; 7,915,026; 7,985,567; 8,097,438; 8,114,645; 8,163,980; 8,257,957; 8,288,147; 8,420,833; 8,535,916; 8,569,023; 8,759,632; 8,765,403; 8,828,684; 8,852,902; 9,040,282; and U.S. Patent Application Pub. Nos. 2015/0087042, 2015/0044747, 2015/0044734, 2014/0370595, 2014/0295517, 2014/0134689, 2014/0038248, 2014/0030789, 2013/0280766, 2013/0267696, 2013/0267012, 2013/0245339, 2013/0115668, 2013/0059295, 2013/0052692, 2012/0288905, 2012/0219998, 2012/0219971, 2012/0190090, 2012/0142979, 2012/0115195, 2011/0229958, 2011/0097769, 2011/0021790, 2011/0014667, 2011/0008829, 2010/0242345, 2010/0218283, 2010/0205855, 2010/0180491, and 2010/0170148 (hereby incorporated by reference in regards in the biosynthetic pathways and/or enzymes, and nucleic acids encoding thereof).

Also described herein, a nucleic acid sequence encoding a synthetic polypeptide comprising an amino acid sequence having at least 70% amino acid sequence identity to SEQ ID NO: 2, wherein said synthetic polypeptide has a xylose import activity, and the amino acid sequence of the polypeptide comprises an amino acid with a polar side chain at position 79. In some embodiments, an expression cassette comprises the nucleic acid sequence operably linked to a promoter.

Also described herein, a method for increasing xylose uptake in an microorganism which comprises introducing into an microorganism at least one heterologous expression cassette operably linked to a promoter that drives expression in the microorganism, said expression cassette comprising a nucleic acid sequence encoding a synthetic polypeptide comprises an amino acid sequence having at least 70% amino acid sequence identity to SEQ ID NO: 2, wherein said synthetic polypeptide has a xylose import activity, and the amino acid sequence of the polypeptide comprises an amino acid with a polar side chain at position 79.

Also described herein, a method for culturing microorganisms capable of using xylose as a carbon source which comprises providing a genetically modified microorganism which comprises a gene encoding a synthetic polypeptide comprising an amino acid sequence having at least 70% amino acid sequence identity to SEQ ID NO: 2, wherein said synthetic polypeptide has a xylose import activity, and the amino acid sequence of the polypeptide which comprises an amino acid with a polar side chain at position 79; and culturing the genetically modified microorganism in a media.

In some embodiments, the media contains a pentose such as xylose, lyxose, ribose, ribulose, xylulose, or arabinose, or a mixture thereof. In some embodiments, the media comprises a mixed carbon source such as a mixture of pentoses and hexoses. In some embodiments, the mixed carbon source is a lignocellulosic biomass such as those from energy crops such as switch grass and elephant grass. Lignocellulosic biomass used in the production of biofuels is composed of carbohydrate polymers (cellulose, hemicellulose) and an aromatic polymer (lignin). Cellulosic materials generally include about 40-60% cellulose, about 20-40% hemicellulose, and 10-30% lignin. The carbohydrate polymers contain different sugar monomers (six carbon sugars (hexoses) and five carbon sugars (pentoses)) that are tightly bound to lignin. In some embodiments, the mixed carbon source is waste biomass. One challenge to biomass fermentation is the high percentage of pentoses in the hemicellulose, such as xylose, or wood sugar which unlike hexoses such as glucose are difficult to ferment.

In some embodiments, the genetically modified microorganism further comprises one or more genetic modifications that improve xylose utilization. In some embodiments, the genetically modified microorganism further comprises one or more motif modifications that reduce glucose repression.

An example of the methods described above is set forth in Example 1 and is not meant to be limiting.

EXAMPLE 1

The following example is intended to be examples of the embodiments disclosed herein, and are not intended to be limiting.

Renewable plant biomass, after saccharification, is typically and primarily a mixture of glucose and xylose. *S. cerevisiae* is a dominant host microbe for industry applications, for the production of a large number of chemicals and commodities including biofuels. Enhancing xylose utilization has been a major focus in *Saccharomyces cerevisiae* strain-engineering efforts. The incentive for these studies arises from the need to use all sugars in the typical mixed-carbon sources that represent standard renewable plant-biomass-based carbon sources. In general, yeast is cultivated solely on glucose. Native yeast has a minor but negligible ability to metabolize xylose, which along with the lack of any native mechanism to uptake xylose, contributes to its sole grown on glucose. While major advances have been made in developing utilization pathways, the efficient import of five carbon sugars into the cell remains an important bottleneck in this endeavor. Regardless of improvements in the xylose utilization pathways, if the cell cannot import the carbon source it cannot use it.

Here we use a semi-engineered *S. cerevisiae* BY4742 strain, engineered with an established xylose utilization pathway, and imposed a laboratory evolution regime with xylose as the sole carbon source. We obtained several evolved strains with improved growth phenotypes and evaluated the best candidate using genome resequencing. We observed remarkably few single nucleotide polymorphisms in the evolved strain, among which we confirmed a single amino acid change in the HXT7 coding sequence to be responsible for the evolved phenotype. The mutant HXT7 (F79S) shows improved xylose uptake rates (Vmax=186.4±20.1 nmol·min$^{-1}$·mg$^{-1}$), and allows the *S. cerevisiae* strain to show significant growth with xylose as the sole carbon source.

In the present study, we used an evolutionary engineering approach to address the problem of xylose import. Starting with a *S. cerevisiae* strain that has been semi-engineered to enhance intracellular xylose consumption, we report the discovery of a mutation in HXT7 that shows improved xylose uptake rates, and allows *S. cerevisiae* to show significant growth with xylose as the sole carbon source. This mutation, F79S, is predicted to lie within the first transmembrane region and is distinct from any mutations discovered to date.

Figure 1B:
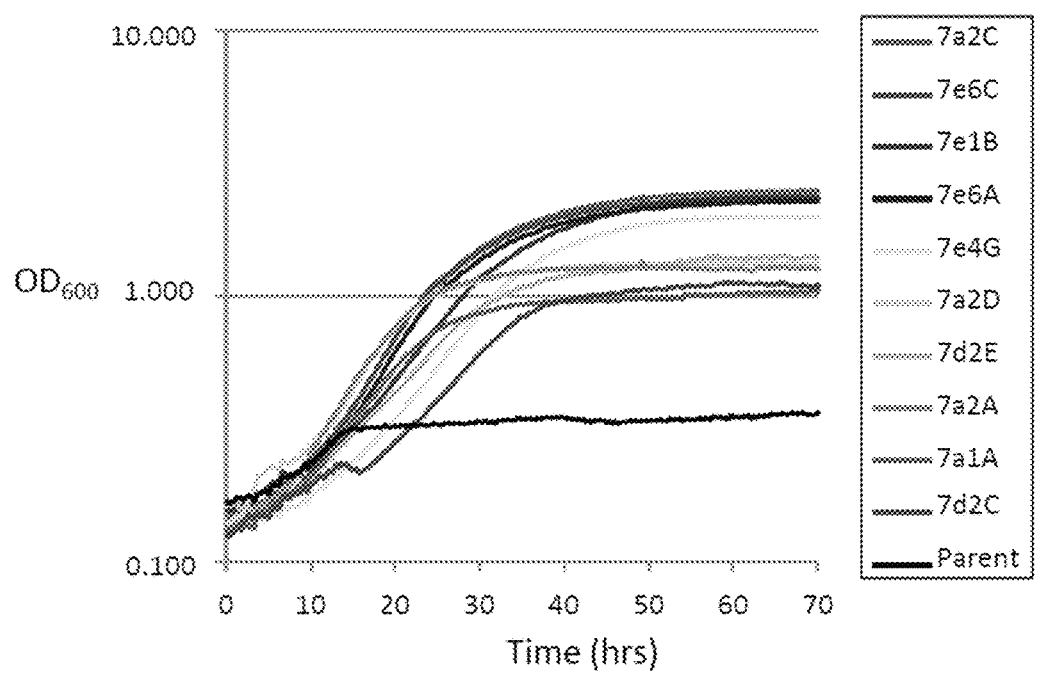
FIG. 1B shows growth curves of the parent strain and fastest growing evolved strains. OD$_{600}$ was measured every 18 minutes for 72 hours. Y-axis is shown in log base 10 scale. The strains in panels FIG. 1A and FIG. 1B were grown on or in SD, 2% xylose media at 30° C.
Figure 1C:
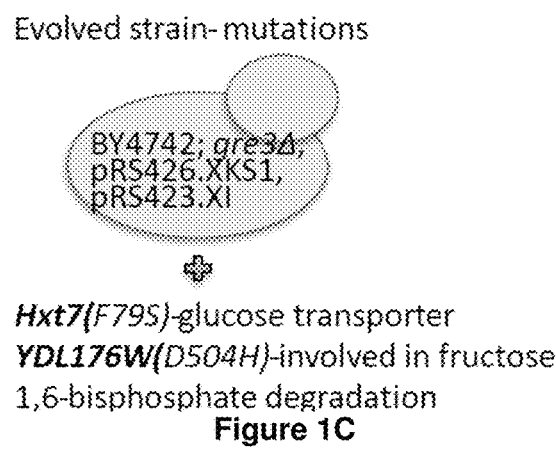
FIG. 1C illustrates genomic sequencing of the evolved strain (JBEI_ScMO002) disclosed the presence of three SNPs, two in coding regions.

Evolution of a xylose utilizing strain. Since xylose import into the cell is a limiting factor in *S. cerevisiae* growth and utilization of xylose, we hypothesized that we could select for increased xylose uptake by subjecting a *S. cerevisiae* strain engineered with an improved cytosolic xylose metabolic pathway to evolution in xylose media (i.e. xylose as the sole carbon source). A BY4742 strain deleted for the XR, gre3, and overexpressing the *Piromyces* sp. xylose isomerase, pspXI, and XKS1 (JBEI_ScMO001) was subcultured in synthetic defined (SD), 2% xylose media. FIGS. 1A, 1B and 1C illustrate an example of laboratory evolution of a xylose utilizing strain. After several rounds of subculturing, the culture was plated onto solid xylose media and the fastest growing colonies were selected (FIG. 1A). The clones were assayed for growth and xylose consumption and the best performing strains were further evolved in SD, 2% xylose. This process was repeated until strains were obtained where growth could be seen in one day. The doubling time of the fastest-growing strains in xylose were reduced to approximately nine hours, down from an initial doubling time of over 150 hours for the unevolved strain (FIG. 1B). Colonies that showed improved xylose utilization were confirmed to be *S. cerevisiae* via 16S sequencing. Other eukaryotic contaminants, such as *Aureobasidium pullulans* were also detected, but not selected for sequencing.

The fastest-growing, xylose-utilizing *S. cerevisiae* strain (JBEI_ScMO002) was selected and analyzed for mutations by whole-genome sequencing. Sequencing revealed single nucleotide polymorphisms (SNPs) in three genes, including a mutation in the hexose transporter, HXT7. Additional mutations were found in YDL176W, a gene predicted to be involved in fructose-1,6-bisphosphatase degradation, as well as in an intergenic region on the left telomere of chromosome eight (FIG. 1C). Because the mutation in chromosome eight was in a heterochromatic region it was not pursued further.

Figure 2A:
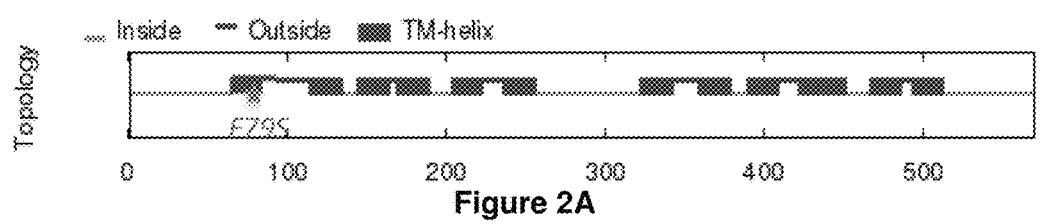
FIG. 2A shows topology prediction of Hxt7 was generated using Spoctopus (36). Red boxes indicate transmembrane regions (12 in total), green lines denoted cytosolic regions, and red lines represent extracellular domains. The Hxt7(F79S) mutation is marked by a blue star, and is predicted to reside in the middle of transmembrane helix one.
Figure 2B:
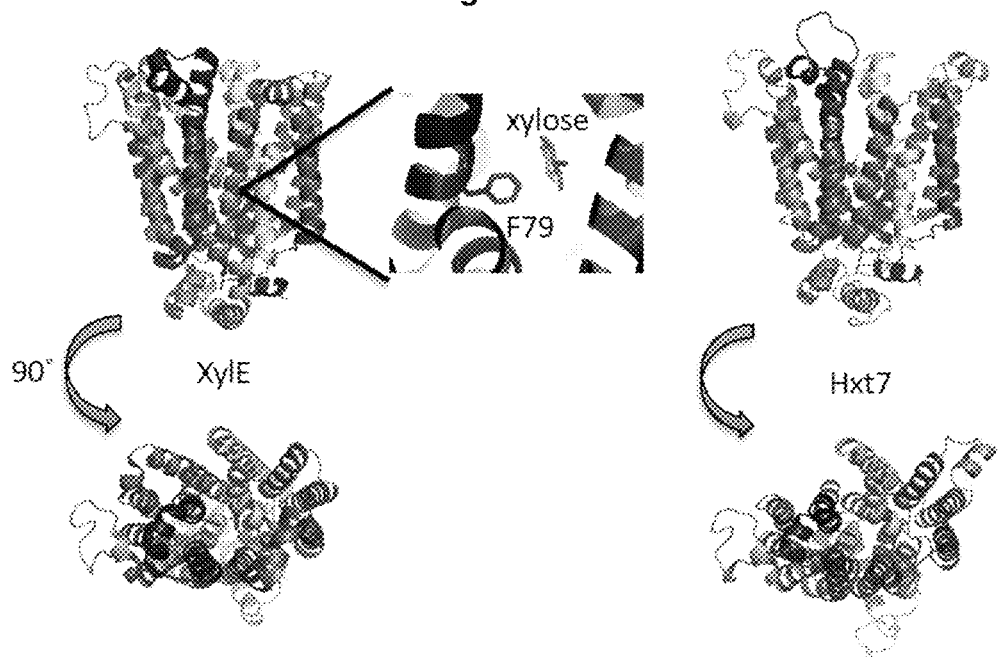
FIG. 2B shows a homology model of the Hxt7 structure. The theoretical structure of Hxt7 was generated from the structure of E. coli XylE with bound xylose (PDB: 4GBY) Left: Side and top view of XylE structure; zoom inset of Phe (pink) homologous to the mutated F79 of Hxt7 in close proximity to xylose (gray). Right: Side and top view of the predicted structure of Hxt7. Each peptide is colored from N (blue) to C-terminus (red).

Hxt7(F79S) confers growth in xylose medium. Since Hxt7 is a known hexose transporter that can also transport pentose sugars with low affinity, the HXT7(F79S) mutation was our most likely candidate for conferring growth in xylose. FIGS. 2A and 2B show an example of structural models of Hxt7. Like other Hxt proteins, SPOCTOPUS software (36) predicted Hxt7 to be a 12-pass transmembrane protein with the F79S mutation located in the first predicted membrane helix (FIG. 2A). Since there is no solved structure for any of the Hxt transport proteins, Phyre software (37) was used to predict the structure of Hxt7 based upon its closest homolog with a solved structure, the bacterial XylE (FIG. 2B). The model predicted that residue F79 resides in the middle of helix one, facing internally towards the central pore. The recently solved structure of XylE has the added benefit that it was crystallized in complex with xylose and glucose, conveying fundamental information about substrate binding (38). Intriguingly, Hxt7 F79 lies in close proximity to the bound-xylose in the pore of the XylE structure, and therefore suggests that the residue is poised to affect xylose binding and transport.

Figure 3:
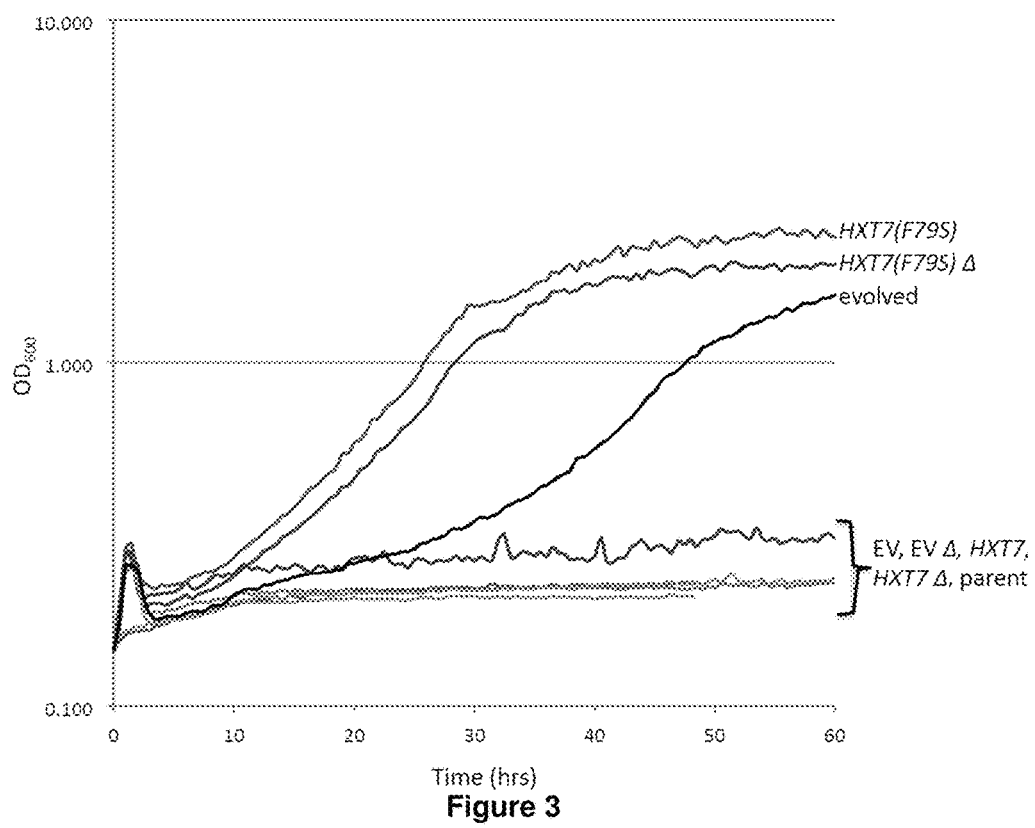
FIG. 3 is an example of a graph showing HXT7(F79S) is responsible for growth on xylose. HXT7, HXT7(F79S) or empty vector (EV) were expressed in strains wild-type (JBEI-9005 EV; JBEI-9006 HXT7(F79S); JBEI-9007 HXT7) or deleted (Δ) for hxt7 (JBEI-9008 EV; JBEI-9009 HXT7(F79S); JBEI-9010 HXT7). The strains were grown in SD, 2% xylose media at 30° C., and the OD$_{600}$ was measured every 15 minutes for 60 hours. Y-axis is shown in log base 10 scale.

To test if the HXT7(F79S) mutation was indeed responsible for the improved growth in xylose, we individually cloned each mutated gene, HXT7(F79S) or YDL176W (D504W), into low-copy plasmids and transformed the resulting plasmids into gre3Δ strains overexpressing pspXI, XKS1, and TAL1. The plasmids were also transformed into a strain that contained additional deletions in the genes of interests (hxt7; ydl176w). The transformants were examined for growth in SD, 2% xylose medium. Both the gre3Δ and gre3Δ hxt7Δ strains expressing HXT7(F79S) grew in xylose medium, reaching a maximum optical density (OD600) of between 2.0-2.4 after 40 hours. The two strains transformed with empty vector plasmids showed no growth after 60 hours (FIG. 3). To eliminate the possibility that an extra copy of HXT7 permits growth in xylose media, wild-type HXT7 was also expressed in the gre3Δ and gre3Δ hxt7Δ strains and tested for growth. The strains did not grow in the xylose medium (FIG. 3), confirming that the xylose growth is specific to the HXT7(F79S) mutation.

Figure 5:
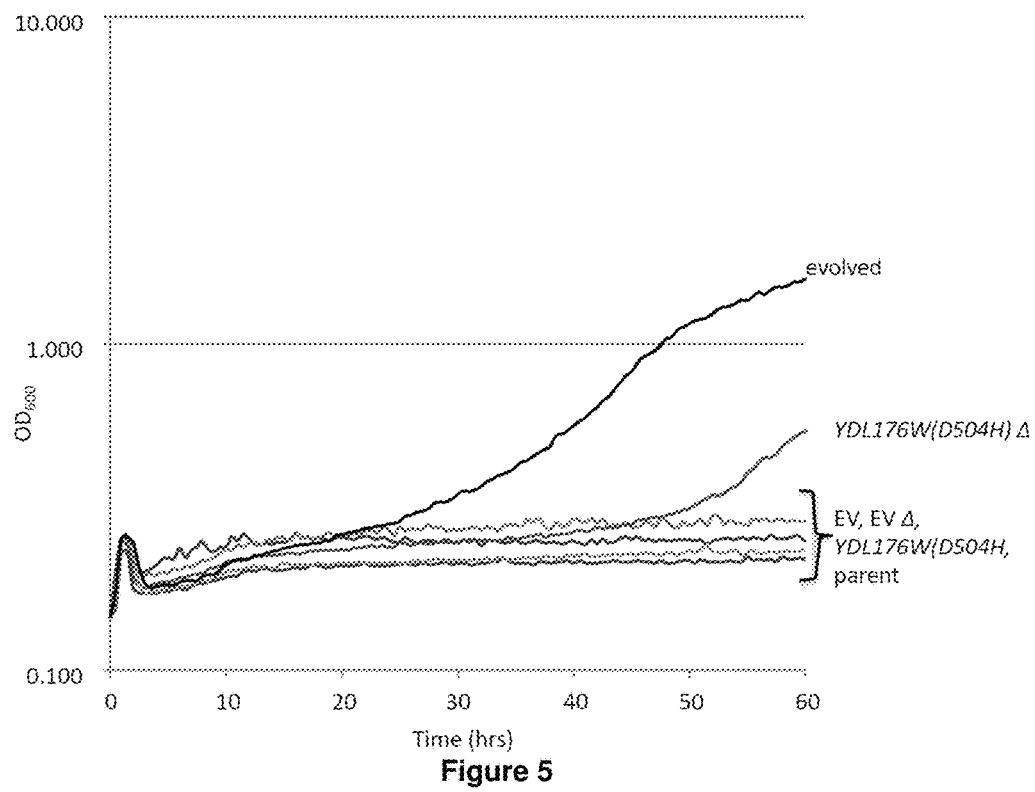
FIG. 5 is an example of a graph showing YDL176W (D504H) does not contribute significantly to growth on xylose. YDL176W(D504H) or empty vector (EV) were expressed in strains wild-type (JBEI-9013 EV; JBEI-9014 YDL176W(D504H)) or deleted (Δ) for ydl176w (JBEI-9015 EV; JBEI-9016 YDL176W(D504H)). The strains were grown in SD, 2% xylose media at 30° C., and the OD$_{600}$ was measured every 15 minutes for 60 hours. Experiment was conducted in triplicate, and representative curved are shown. For YDL176W(D504H) (green), only two of the three clones showed growth. Y-axis is shown in log base 10 scale.

YDL176W(D504H) did not contribute significantly to the growth of the evolved strain in xylose. Strains expressing the YDL176W(D504H) alone showed no growth in SD, 2% xylose medium, while strains expressing YDL176W (D504H) along with a wild-type genomic copy only showed marginal growth to OD 0.6 after 60 hours (FIG. 5).

Figure 6:
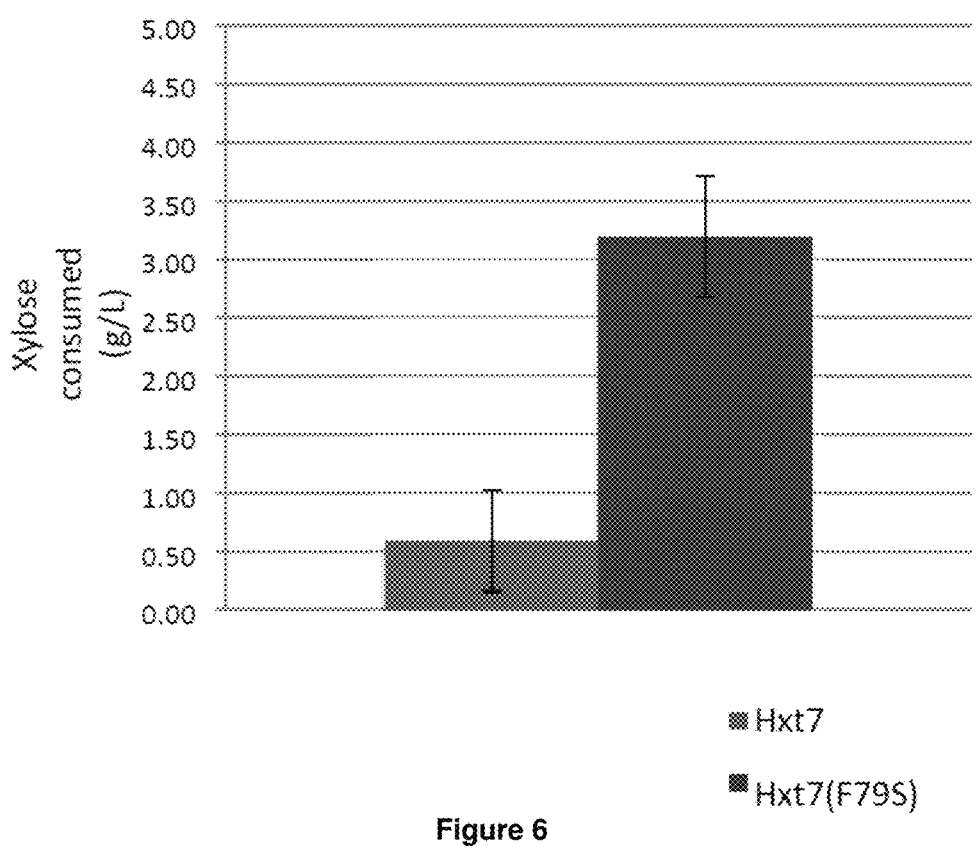
FIG. 6 is an example of a graph showing HXT7(F79S) is responsible for xylose uptake. Strains expressing HXT7 (JBEI-9010) or HXT7(F79S) (JBEI-9009) were grown at 30° C., and the amount of xylose consumed from SD, 2% xylose media was examined after 48 hours.

Finally, to verify that the growth seen in the HXT7(F79S) strains were indeed due to increased xylose uptake, the amount of xylose consumed from the media was examined after 48 hours. High-performance liquid chromatography (HPLC) analysis established that strains expressing wild-type HXT7 only consumed 0.5±0.4 g/L xylose, while strains expressing the mutant HXT7F79S consumed 3.2±0.5 g/L (FIG. 6), corroborating that the growth seen in HXT7F79S expressing strains is due to increased xylose uptake.

Figure 4:
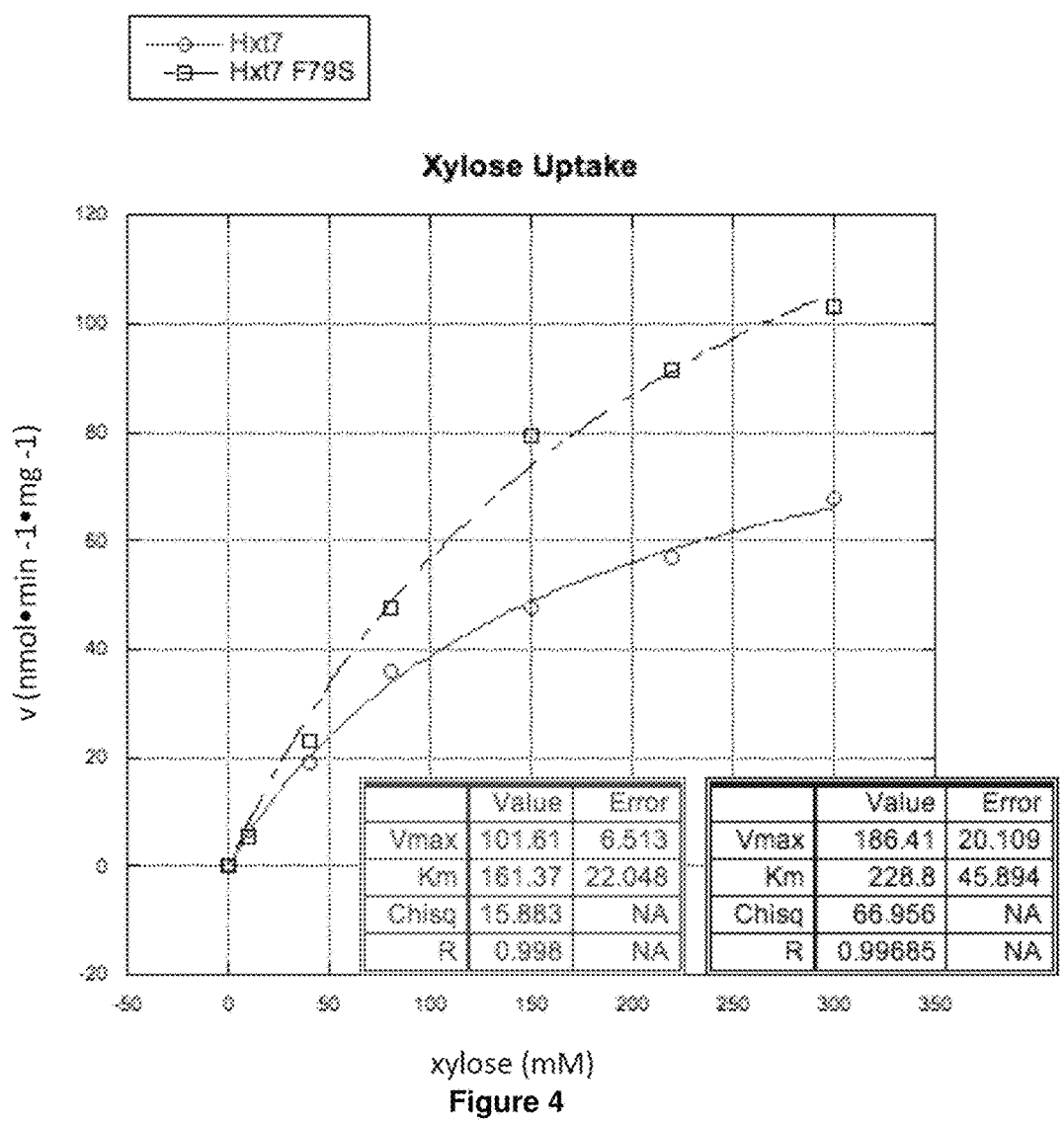
FIG. 4 is an example of a graph showing Xylose uptake kinetics of S. cerevisiae strains expressing HXT7, or HXT7 (F79S). Initial xylose uptake (10 s) was measured at 30° C. over a concentration range of 10 to 300 mM xylose. To arrive at Michaelis-Menton kinetic parameters, global curve fitting analysis was applied to the mean of three independent measurements at each concentration for both HXT7 (solid line, open circle; JBEI-9012), and HXT7(F79S) (dashed line, open square; JBEI-9011).

Kinetic measurement of Hxt7 and Hxt7(F79S) mutant. In order to understand how HXT7(F79S) affected transport, the kinetic properties of the mutant and wild-type transporters were assayed with radioactive sugar uptake assays (FIG. 4). Strains deleted for all hexose transporters that can transport xylose (hxt1Δ, hxt2Δ, hxt4Δ, hxt5Δ, hxt7Δ, gal2Δ) were transformed with low-copy plasmids expressing either HXT7 or HXT7(F79S). The wild-type Hxt7 transporter was confirmed to be a low-affinity xylose transporter with a Km of 161.4±22 mM, and a Vmax of 101.6±6.5 nmol·min$^{-1}$·mg$^{-1}$ for xylose, similar to previously published values (22, 35). The Hxt7(F79S) mutant transporter displayed a similar xylose substrate affinity of 228.8±45.9 mM, but showed about a two-fold increase in xylose transport velocity (Vmax=186.4±20.1 nmol·min$^{-1}$·mg$^{-1}$) over its wild-type counterpart.

Materials and Methods

Strains and media. A complete list of strains and plasmids used in this study can be found in Tables 1 and 2, and are available through the JBEI registry (http://public-registry.jbei.org (39). Yeast cells were grown in standard rich (yeast extract-peptone) or synthetic defined media (SD, yeast nitrogen base with CSM amino acids (Sunrise Science Products) for plasmid selection) with 2% sugar, unless otherwise stated. For yeast kanamycin resistance selection, 250 ug/ml of geneticin (G418) was used in rich medium. Bacteria were grown in LB with 50 ug/ml carbenicillin.

*S. cerevisiae* strains were transformed with plasmids using the conventional lithium acetate method (40). DNA cloning was performed using standard techniques; T4 DNA polymerase-mediated (Fermentas) ligations or Gibson assembly in *Escherichia coli*, or homologous recombination in *S. cerevisiae*. Plasmids were recovered from *S. cerevisiae* by lysing the cells mechanically with glass beads, followed by plasmid mini-prep (Qiagen). Chromosomal gene deletions were generated by integration of PCR products flanked by loxP sites (41).

Strain evolution. A BY4742 gre3Δ strain expressing *Piromyces* sp. XI (Pi-xylA), and XKS1 from two high-copy plasmids was evolved in SD, -URA-HIS with 2% xylose. The 4 mL culture was maintained at 30° C., shaking at 200 revolutions/min. Mutants with increased specific growth rates were selected through dilution of the culture when turbidity was seen. At period intervals, the culture(s) were plated onto solid SD-URA-HIS, 2% xylose medium, and several of the fastest-growing colonies were selected for independent evolution in liquid culture. This process was repeated, selecting for the fastest growing isolates at each round, until culture saturation was achieved within one to two days of dilution. In total, the evolution process took approximately three months until satisfactory growth was achieved. At the end of the process, about one dozen clones were re-streaked and tested individually for xylose growth. One of the best performing clones, 7a2c (JBEI_ScMO002), was selected and prepared for genome sequencing.

Genome sequencing. Five μg of total gDNA was extracted from the parental and evolved strains, and sent to the Department of Energy Joint Genome Institute (DOE JGI, Walnut creek) for whole genome resequencing. Burrows-Wheeler Aligner (BWA) was used to align reads, and Bcftools to assign SNPs and indels. Sequencing files were analyzed using Integrated Genome Viewer software (42).

Xylose growth experiments. Strains were grown overnight in SD-LEU-URA 1.4% glucose, 0.6% xylose medium. Cells were pelleted and resuspended to a final OD600 of 0.1 in 1 mL of SD-LEU-URA 2% xylose medium in a 24-well plate. The plate was then placed into the BioTek Synergy 4, preheated to 30° C., and the growth was monitored by taking the OD600 every fifteen minutes, for 60 hours.

Analysis of xylose concentrations. The concentrations of sugars were quantified on an Agilent Technologies 1200 series HPLC equipped with an Aminex H column. Samples were filtered through 0.45 μm VWR filters to remove cells, and 5 μl of each sample was injected onto the column, preheated to 50° C. The column was eluted with 4 mM $H_2SO_4$ at a flow rate of 600 μl/min for 25 min. Sugars were monitored by refractive index detector, and concentrations were calculated by comparison of peak areas to known standards.

Radioactive sugar uptake. Uptake of 14C-xylose was used to determine the Michaelis-Menten parameters for Hxt7 (F79S). 1-14C-xylose was purchased from American Radiolabeled Chemicals. Twelve mL overnight cultures grown in SD-URA medium with 1.4% glucose 0.6% xylose were diluted to an OD600 of 0.1/ml in 50 mL of media and allowed to grow until mid-log phase (OD600 0.5 to 0.8). 20 ODs of cells were centrifuged at 3000×g for 5 min and washed once with 10 mL of 0.1 M potassium phosphate buffer, pH 6.8. Cultures were then resuspended in 300 μl of 0.1 M potassium phosphate buffer, pH 6.8, and warmed to 30° C. 25 ul of cells were then mixed with an equal amount of radiolabeled sugar solutions, producing final mixed sugar concentrations between 10 mM and 400 mM. Ten seconds after mixing, the samples were filtered through 0.2 μm Whatman Nuclepore filters (GE Healthcare), and washed with 10 mL ice-cold 0.1 M potassium phosphate, 500 mM xylose buffer. Filters were subsequently placed in 4 mL Ecoscint XR scintillation fluid (National Diagnostics) and counted in a LS 6500 scintillation counter (Beckman-Coulter). KaleidaGraph software (Synergy Software) was used to plot the data, and to arrive at Michaelis-Menten kinetic parameters for each transporter. All assays were performed in biological triplicate. One outlier with accelerated uptake was discarded from the 300 mM HXT7(F79S) data set.

Protein structure prediction. The predicted Hxt7 structure (FIG. 2B) was generated using Phyre (37), and the published XylE structures (PDB: 4GBY and 4GBZ). Three-dimensional, structural images were created with PyMOL (Schrödinger, LLC.).

Discussion

The need to engineer a *S. cerevisiae* strain that can consume both pentose and hexose sugars, ideally together, is well recognized as important for engineering yeast to produce fuels and commodity chemicals. The main impediment to the realization of this goal is the lack of necessary xylose transporters in *S. cerevisiae*. Specifically, two aspects of xylose transport need improvement before the goal of co-utilization can be reached: (1) transport rates, (2) glucose inhibition. The latter problem has been recently addressed using an elegant selection approach to generate glucose insensitive Gal2 and Hxt7 variants (35). Here we show the generation of an endogenous xylose transporter that has high rates of transport while maintaining high growth rates on xylose.

In our efforts we compiled several commonly used cytosolic xylose utilization genes and genetic modifications that served as our semi-engineered strain and as the basal strain for lab evolution (FIG. 1A). A lab evolution regime, using serial dilution and plating on solid medium, and 2% xylose as the sole carbon source led to the appearance of colonies that could sustain significant growth on the xylose sugar (FIG. 1B). The phenotype was tracked to a single mutation in the Hxt7 protein and is distal and different from all the mutations tracked to this protein to date. The HXT7(F79S) mutation allows for an improvement in xylose transport rates (Vmax), as well as provides for growth on xylose.

Lab evolution of *S. cerevisiae* is a commonly used strategy to obtain variants that have improved xylose utilization phenotypes. Several such studies are reported in the literature and each has resulted in the identification of key metabolic and regulatory genes (43-47). Our study is the first lab evolution to find a mutation in a plasma membrane sugar transporter (HXT7), highlighting the importance of selecting appropriate starting strains and selective pressures to obtain desired phenotypes. While evolutionary selection is a powerful approach, it cannot sample all possible mutations in the amount of time given in the lab. Directed evolution approaches have produced heterologous transporters with improved kinetics, such as the *Candida intermedia* Gxs1 pump, and the Scheffersomyces stipitus Xut3 transporter (48), and may be a good next step for further HXT7 engineering.

Native *S. cerevisiae* sugar transporters all have much greater specificity and uptake rates for C6 sugars. Several of the native C6 transporters can leak in xylose, and the one with the best xylose specificity, Hxt7, only displays a Km of 161 mM. Hxt7 also exhibits a meager uptake rate of 101 nmol·min$^{-1}$·mg$^{-1}$, does not alone support growth on xylose, and is inhibited by the presence of other sugars (22). Some heterologous xylose-transporters have been identified, and have helped improve xylose utilization (31). However, their performance has been hampered by reduced growth rates, problems with substrate affinities, transport rates, or substrate inhibition. Recently success in engineering of native transporters has resulted in the identification of a xylose transport sequence motif (34), and the generation of glucose insensitive strains (35). These approaches also resulted in diminished uptake rates (Vmax), and resulted in modest growth on xylose, which are not advantageous to future mixed sugar co-utilization. The HXT7(F79S) mutation alone enhanced the xylose transport rate (Vmax), which enables growth on xylose in a minimally engineered background strain. The mutation decreases doubling times from over 150 hours to nine hours (FIG. 1B), and doubles xylose transport rates to 186.4 nmol·min$^{-1}$·mg$^{-1}$ (FIG. 4), without affecting xylose affinity.

Using the structure of the bacterial homolog of the yeast Hxt proteins, XylE (38), we were able to predict the structure of Hxt7 (FIG. 2B), and to address possible mechanisms of action for Hxt7(F79S). The model predicts that the mutated residue, F79, faces inward towards the central sugar-binding pore. The mutated Phenylalanine (Phe) residue of Hxt7 aligns with a Phe residue that participates in xylose binding for XylE, providing support for the importance of this residue in Hxt7 sugar transport. The amino acid substitution from a Phe to a Serine (Ser) shifts the Hxt7 sugar-transporting pore towards polarity. This perhaps provides for increased xylose transport rates by allowing for additional hydrogen bonding between Ser and xylose; by allowing for additional water molecules to enter, thereby contributing to substrate binding through water-mediated hydrogen binding; or by allowing for a conformational change that favors xylose transport. Because we do not observe an increase in xylose affinity (Km) with Hxt7 (F79S), the latter two mechanisms are more likely. Further structural information for the yeast Hxt proteins will enhance our understanding of xylose transport, and help to solidify the exact mechanism of how the HXT7(F79S) mutation affects xylose transport.

Both of the mutations found in the evolved strain were reasonable candidates for impacting sugar utilization. The native HXT7 transporter had been previously shown to provide for the highest intracellular accumulation of xylose in S. cerevisiae (26). The only other mutation in our xylose evolved strain, YDL176W(D504H), had an almost indiscernible impact on this phenotype by itself (FIG. 5). Although YDL176W is largely uncharacterized, it is predicted to be involved in fructose-1,6-bisphosphatase (Fbp1) degradation and a member of the glucose-induced degradation (GID) complex (49-51), making it a likely target for affecting sugar utilization. When S. cerevisiae are starved of glucose for prolonged periods of time, gluconeogenic enzymes such as Fbp1 are induced (52). Therefore, one possible explanation for this mutation is that it resulted not from the adaptation to xylose, but instead from long-term glucose starvation. Alternatively, components of the GID complex have been implicated in degradation of Hxt7 (53). Perhaps Ydl176W(D504H) could be altering the degradation of Hxt7, explaining the slight growth improvement seen at 60 hours (FIG. 5).

This invention has very broad applicability. All industries and research ventures that use S. cerevisiae yeast microbial hosts as their platform to convert sugar to a desired product may find this mutant transporter useful. Moreover, the xylose utilization phenotype reported here is due to a single nucleotide substitution, making this discovery easily transferable to established industrial strains. The HXT7(F79S) mutation allows yeast to better use xylose, thus allowing it to use the main sugars (glucose and xylose) present in the mixes that arise from saccharification of plant biomass. This ability would be desirable specifically to industries and ventures that are manufacturing bulk compounds and chemicals and that wish to have inexpensive and sustainable biomass as the feedstock.

TABLE 1

S. cerevisiae strains used in this work

| Name | Genotype | Source |
|---|---|---|
| JBEI_ScMO001 | BY4742; gre3Δ pRS426.XKS1 pRS423.XI | This study |
| JBEI_ScMO002 | BY4742; gre3Δ pRS426.XKS1 pRS423.XI xylose evolved | This study |
| JBEI-9005 | BY4742; gre3Δ pMOXYL3 pRS416 | This study |
| JBEI-9006 | BY4742; gre3Δ pMOXYL3 pRS416.HXT7(F79S) | This study |
| JBEI-9007 | BY4742; gre3Δ pMOXYL3 pRS416.HXT7 | This study |
| JBEI-9008 | BY4742; gre3Δ hxt7Δ::loxpKanMX pMOXYL3 pRS416 | This study |
| JBEI-9009 | BY4742; gre3Δ hxt7Δ::loxpKanMX pMOXYL3 pRS416.HXT7(F79S) | This study |
| JBEI-9010 | BY4742; gre3Δ hxt7Δ::loxpKanMX pMOXYL3 pRS416.HXT7 | This study |
| JBEI-9011 | BY4742; hxt1Δ::loxp hxt2Δ::loxpLEU2 hxt4ΔKanMX hxt5Δ::loxp hxt7Δ::loxp gal2Δ::loxp pRS416.HXT7(F79S) | This study |
| JBEI-9012 | BY4742; hxt1Δ::loxp hxt2Δ::loxpLEU2 hxt4ΔKanMX hxt5Δ::loxp hxt7Δ::loxp gal2Δ::loxp pRS416.HXT7 | This study |
| JBEI-9013 | BY4742; gre3Δ; pMOXYL3 pRS413 | This study |
| JBEI-9014 | BY4742; gre3Δ pMOXYL3 pRS413.YDL176W(D504H) | This study |
| JBEI-9015 | BY4742; gre3Δ ydl176wΔloxpKanMX pMOXYL3 pRS413 | This study |
| JBEI-9016 | BY4742; gre3Δ ydl176wΔloxpKanMX pMOXYL3 pRS413.YDL176W(D504H) | This study |

TABLE 2

Description of plasmids used in this work

| Name | Description | Source |
|---|---|---|
| pRS426.XKS1 | High copy, URA3 plasmid, expressing XKS1 under control of a TDH3p and a CYC1t | This study |
| pRS423.XI | High copy, HIS3 plasmid, expressing yeast codon optimized, piromyces species XI under control of a TDH3p and a CYC1t | This study |
| pMOXL3 | High copy, Leu2d plasmid, expressing TAL1 under control of a TEF1p and a ADH1t, and XKS1 and piromyces species X1, separately under control of a TDH3p and a CYC1t | This study |
| pRS416 | Empty, low copy, URA3 plasmid | |
| pRS413 | Empty, low copy, HIS3 plasmid | |
| pRS416.HXT7 (F79S) | pRS416, expressing HXT7(F79S) under control of 500bp of its native promoter and terminator | This study |
| pRS416.HXT7 | pRS416, expressing HXT7 under control of 500 bp of its native promoter and terminator | This study |
| pRS413.YDL176W (D504H) | pRS413, expressing YDL176W(D504H) under control of 500bp of its native promoter and terminator | This study |

In the foregoing specification, the invention has been described with reference to specific embodiments. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of invention.

REFERENCES CITED

1. Keasling J D (2010) Manufacturing Molecules Through Metabolic Engineering. Science 330:1355-1358.
2. Zhang F, Rodriguez S, Keasling J D (2011) Metabolic engineering of microbial pathways for advanced biofuels production. Current Opinion in Biotechnology 22:775-783.
3. Hong K-K, Nielsen J (2012) Metabolic engineering of Saccharomyces cerevisiae: a key cell factory platform for future biorefineries. Cell Mol Life Sci 69:2671-2690.
4. Nielsen J, Larsson C, van Maris A, Pronk J (2013) Metabolic engineering of yeast for production of fuels and chemicals. Current Opinion in Biotechnology 24:398-404.
5. Gírio F M, Fonseca C, Carvalheiro F, Duarte L C (2010) Hemicelluloses for fuel ethanol: A review. Bioresource . . . .
6. Young E, Lee S M, Alper H (2010) Optimizing pentose utilization in yeast: the need for novel tools and approaches. Biotechnology for Biofuels.
7. Kuyper M et al. (2005) Metabolic engineering of a xylose-isomerase-expressing Saccharomyces cerevisiae strain for rapid anaerobic xylose fermentation. FEMS Yeast Research 5:399-409.
8. Kuyper M et al. (2003) High-level functional expression of a fungal xylose isomerase: the key to efficient ethanolic fermentation of xylose by Saccharomyces cerevisiae? FEMS Yeast Research 4:69-78.
9. Walfridsson M et al. (1996) Ethanolic fermentation of xylose with Saccharomyces cerevisiae harboring the Thermus thermophilus xylA gene, which expresses an active xylose (glucose) isomerase. Applied and Environmental Microbiology 62:4648-4651.
10. Madhavan A et al. (2009) Xylose isomerase from polycentric fungus Orpinomyces: gene sequencing, cloning, and expression in Saccharomyces cerevisiae for bioconversion of xylose to ethanol. Appl Microbiol Biotechnol 82:1067-1078.
11. Brat D, Boles E, Wiedemann B (2009) Functional expression of a bacterial xylose isomerase in Saccharomyces cerevisiae. Applied and Environmental Microbiology 75:2304-2311.
12. Kötter P, Amore R, Hollenberg C P, Ciriacy M (1990) Isolation and characterization of the Pichia stipitis xylitol dehydrogenase gene, XYL2, and construction of a xylose-utilizing Saccharomyces cerevisiae transformant. Curr Genet 18:493-500.
13. Ho N W, Chen Z, Brainard A P (1998) Genetically engineered Saccharomyces yeast capable of effective cofermentation of glucose and xylose. Applied and Environmental Microbiology 64:1852-1859.
14. Toivari M H, Aristidou A, Ruohonen L, Penttilä M (2001) Conversion of xylose to ethanol by recombinant Saccharomyces cerevisiae: importance of xylulokinase (XKS1) and oxygen availability. Metabolic Engineering 3:236-249.
15. Lee T-H et al. (2003) Effects of xylulokinase activity on ethanol production from D-xylulose by recombinant Saccharomyces cerevisiae. J Appl Microbiol 95:847-852.
16. Walfridsson M, Hallborn J, Penttilä M, Keränen S, Hahn-Hägerdal B (1995) Xylose-metabolizing Saccharomyces cerevisiae strains overexpressing the TKL1 and TAL1 genes encoding the pentose phosphate pathway enzymes transketolase and transaldolase. Applied and Environmental Microbiology 61:4184-4190.
17. Jin Y-S, Alper H, Yang Y-T, Stephanopoulos G (2005) Improvement of xylose uptake and ethanol production in recombinant Saccharomyces cerevisiae through an inverse metabolic engineering approach. Applied and Environmental Microbiology 71:8249-8256.
18. Wahlbom C F, Cordero Otero R R, van Zyl W H, Hahn-Hägerdal B, Jönsson L J (2003) Molecular analysis of a Saccharomyces cerevisiae mutant with improved ability to utilize xylose shows enhanced expression of proteins involved in transport, initial xylose metabolism, and the pentose phosphate pathway. Applied and Environmental Microbiology 69:740-746.
19. Latimer L N et al. (2014) Employing a combinatorial expression approach to characterize xylose utilization in Saccharomyces cerevisiae. Metabolic Engineering 25:20-29.
20. Parachin N S, Gorwa-Grauslund M F (2011) Isolation of xylose isomerases by sequence- and function-based screening from a soil metagenomic library. Biotechnology for Biofuels 4:9.
21. Hamacher T, Becker J, Gárdonyi M, Hahn-Hägerdal B, Boles E (2002) Characterization of the xylose-transporting properties of yeast hexose transporters and their influence on xylose utilization. Microbiology (Reading, Engl) 148:2783-2788.
22. Saloheimo A A et al. (2007) Xylose transport studies with xylose-utilizing Saccharomyces cerevisiae strains expressing heterologous and homologous permeases. Appl Microbiol Biotechnol 74:1041-1052.
23. Gárdonyi M, Jeppsson M, Lidén G, Gorwa-Grauslund M F, Hahn-Hägerdal B (2003) Control of xylose consumption by xylose transport in recombinant Saccharomyces cerevisiae. Biotechnol Bioeng 82:818-824.
24. Leandro M J, Fonseca C S, GonÃalves P (2009) Hexose and pentose transport in ascomycetous yeasts: an overview. FEMS Yeast Research 9:511-525.
25. Wahlbom C F, van Zyl W H, Jönsson L J, Hahn-Hägerdal B, Otero R R C (2003) Generation of the improved recombinant xylose-utilizing Saccharomyces cerevisiae TMB 3400 by random mutagenesis and physiological comparison with Pichia stipitis CBS 6054. FEMS Yeast Research 3:319-326.
26. Sedlak M, Ho N W Y (2004) Characterization of the effectiveness of hexose transporters for transporting xylose during glucose and xylose co-fermentation by a recombinant Saccharomyces yeast. Yeast 21:671-684.
27. Subtil T, Boles E (2012) Competition between pentoses and glucose during uptake and catabolism in recombinant Saccharomyces cerevisiae. Biotechnology for Biofuels 5:14.
28. Weierstall T, Hollenberg C P, Boles E (1999) Cloning and characterization of three genes (SUT1-3) encoding glucose transporters of the yeast Pichia stipitis. Mol Microbiol 31:871-883.
29. Leandro M J, Gonçalves P, Spencer-Martins I (2006) Two glucose/xylose transporter genes from the yeast Candida intermedia: first molecular characterization of a yeast xylose-H+ symporter. Biochem J 395:543.
30. Hector R E, Qureshi N, Hughes S R, Cotta M A (2008) Expression of a heterologous xylose transporter in a Saccharomyces cerevisiae strain engineered to utilize xylose improves aerobic xylose consumption. Appl Microbiol Biotechnol 80:675-684.

31. Runquist D, Hahn-Hägerdal B, Rådström P (2010) Comparison of heterologous xylose transporters in recombinant *Saccharomyces cerevisiae*. Biotechnology for Biofuels 3:5.
32. Du J, Li S, Zhao H (2010) Discovery and characterization of novel d-xylose-specific transporters from *Neurospora crassa* and *Pichia stipitis*. Mol Biosyst 6:2150-2156.
33. Young E, Poucher A, Comer A, Bailey A, Alper H (2011) Functional survey for heterologous sugar transport proteins, using *Saccharomyces cerevisiae* as a host. Applied and Environmental Microbiology 77:3311-3319.
34. Young E M, Tong A, Bui H, Spofford C, Alper H S (2014) Rewiring yeast sugar transporter preference through modifying a conserved protein motif. Proc Natl Acad Sci USA 111:131-136.
35. Farwick A, Bruder S, Schadeweg V, Oreb M, Boles E (2014) Engineering of yeast hexose transporters to transport d-xylose without inhibition by d-glucose. Proceedings of the . . . .
36. Viklund H, Bernsel A, Skwark M, Elofsson A (2008) SPOCTOPUS: a combined predictor of signal peptides and membrane protein topology. BIOINFORMATICS 24:2928-2929.
37. Kelley L A, Sternberg M J E (2009) Protein structure prediction on the Web: a case study using the Phyre server. Nat Protoc 4:363-371.
38. Sun L et al. (2012) Crystal structure of a bacterial homologue of glucose transporters GLUT1-4. Nature 490:361-366.
39. Ham T S et al. (2012) Design, implementation and practice of JBEI-ICE: an open source biological part registry platform and tools. Nucleic Acids Res 40:e141.
40. Gietz R D, Woods R A (2002) Transformation of yeast by lithium acetate/single-stranded carrier DNA/polyethylene glycol method. Meth Enzymol 350:87-96.
41. Fang F et al. (2011) A vector set for systematic metabolic engineering in *Saccharomyces cerevisiae*. Yeast 28:123-136.
42. Robinson J T et al. (2011) Integrative genomics viewer. Nature Biotechnology 29:24-26.
43. Sato T K et al. (2014) Harnessing Genetic Diversity in *Saccharomyces cerevisiae* for Fermentation of Xylose in Hydrolysates of Alkaline Hydrogen Peroxide-Pretreated Biomass. Applied and Environmental Microbiology 80:540-554.
44. Zha J, Shen M, Hu M, Song H, Yuan Y (2014) Enhanced expression of genes involved in initial xylose metabolism and the oxidative pentose phosphate pathway in the improved xylose-utilizing *Saccharomyces cerevisiae* through evolutionary engineering. J Ind Microbiol Biotechnol 41:27-39.
45. Kim S R et al. (2013) Rational and Evolutionary Engineering Approaches Uncover a Small Set of Genetic Changes Efficient for Rapid Xylose Fermentation in *Saccharomyces cerevisiae*. PLoS ONE 8:e57048.
46. Shen Y et al. (2012) An efficient xylose-fermenting recombinant *Saccharomyces cerevisiae* strain obtained through adaptive evolution and its global transcription profile. Appl Microbiol Biotechnol.
47. Zhou H, Cheng J-S, Wang B, Fink G R, Stephanopoulos G (2012) Xylose isomerase overexpression along with engineering of the pentose phosphate pathway and evolutionary engineering enable rapid xylose utilization and ethanol production by *Saccharomyces cerevisiae*. Metabolic Engineering.
48. Young E M, Comer A D, Huang H, Alper H S (2012) A molecular transporter engineering approach to improving xylose catabolism in *Saccharomyces cerevisiae*. Metabolic Engineering 14:401-411.
49. Kourmpetis Y A I, van Dijk A D J, Bink M C A M, van Ham R C H J, Braak ter C J F (2010) Bayesian Markov Random Field analysis for protein function prediction based on network data. PLoS ONE 5:e9293.
50. Ulitsky I, Shlomi T, Kupiec M, Shamir R (2008) From E-MAPs to module maps: dissecting quantitative genetic interactions using physical interactions. Molecular Systems Biology 4:209.
51. Pitre S et al. (2006) PIPE: a protein-protein interaction prediction engine based on the re-occurring short polypeptide sequences between known interacting protein pairs. BMC Bioinformatics 7:365.
52. Barnett J A, Entian K-D (2005) A history of research on yeasts 9: regulation of sugar metabolism. Yeast 22:835-894.
53. Snowdon C, Hlynialuk C, van der Merwe G (2008) Components of the Vid30c are needed for the rapamycin-induced degradation of the high-affinity hexose transporter Hxt7p in *Saccharomyces cerevisiae*. FEMS Yeast Research 8:204-216.

What is claimed is:

1. A synthetic polypeptide comprising an amino acid sequence identical to SEQ ID NO: 2 except there is an amino acid with a polar side chain at position 79 and wherein said synthetic polypeptide has a xylose import activity.

2. The synthetic polypeptide of claim 1, wherein the amino acid with a polar side chain is selected from the group consisting of: glycine, serine, threonine, cysteine, tyrosine, asparagine, glutamine, lysine, arginine, histidine, aspartic acid, and glutamine acid.

3. The synthetic polypeptide of claim 2, wherein the amino acid with a polar side chain is serine.

4. The synthetic polypeptide of claim 1, wherein the xylose import activity has a Vmax having a value within from 166.30 to 206.52 nmol·min$^{-1}$·mg$^{-1}$ and a Km having a value within from 182.9 to 274.7 mM.

5. The synthetic polypeptide of claim 4, wherein the xylose import activity has a Vmax having a value of at least 186.41 nmol·min$^{-1}$·mg$^{-1}$ and a Km having a value of at least 228.8 mM.

* * * * *

SEQUENCE LISTING

```
<160> NUMBER OF SEQ ID NOS: 4

<210> SEQ ID NO 1
<211> LENGTH: 570
<212> TYPE: PRT
<213> ORGANISM: Saccharomyces cerevisiae

<400> SEQUENCE: 1

Met Ser Gln Asp Ala Ala Ile Ala Glu Gln Thr Pro Val Glu His Leu
1               5                   10                  15

Ser Ala Val Asp Ser Ala Ser His Ser Val Leu Ser Thr Pro Ser Asn
            20                  25                  30

Lys Ala Glu Arg Asp Glu Ile Lys Ala Tyr Gly Glu Gly Glu Glu His
        35                  40                  45

Glu Pro Val Val Glu Ile Pro Lys Arg Pro Ala Ser Ala Tyr Val Thr
    50                  55                  60
```

-continued

```
Val Ser Ile Met Cys Ile Met Ile Ala Phe Gly Gly Phe Val Phe Gly
 65                  70                  75                  80

Trp Asp Thr Gly Thr Ile Ser Gly Phe Ile Asn Gln Thr Asp Phe Ile
                 85                  90                  95

Arg Arg Phe Gly Met Lys His Lys Asp Gly Thr Asn Tyr Leu Ser Lys
                100                 105                 110

Val Arg Thr Gly Leu Ile Val Ser Ile Phe Asn Ile Gly Cys Ala Ile
                115                 120                 125

Gly Gly Ile Ile Leu Ser Lys Leu Gly Asp Met Tyr Gly Arg Lys Val
130                 135                 140

Gly Leu Ile Val Val Val Ile Tyr Ile Gly Ile Ile Ile Gln
145                 150                 155                 160

Ile Ala Ser Ile Asn Lys Trp Tyr Gln Tyr Phe Ile Gly Arg Ile Ile
                165                 170                 175

Ser Gly Leu Gly Val Gly Gly Ile Ala Val Leu Ser Pro Met Leu Ile
                180                 185                 190

Ser Glu Val Ser Pro Lys His Leu Arg Gly Thr Leu Val Ser Cys Tyr
                195                 200                 205

Gln Leu Met Ile Thr Ala Gly Ile Phe Leu Gly Tyr Cys Thr Asn Phe
210                 215                 220

Gly Thr Lys Asn Tyr Ser Asn Ser Val Gln Trp Arg Val Pro Leu Gly
225                 230                 235                 240

Leu Cys Phe Ala Trp Ala Leu Phe Met Ile Gly Gly Met Thr Phe Val
                245                 250                 255

Pro Glu Ser Pro Arg Tyr Leu Ala Glu Val Gly Lys Ile Glu Glu Ala
                260                 265                 270

Lys Arg Ser Ile Ala Val Ser Asn Lys Val Ala Val Asp Asp Pro Ser
                275                 280                 285

Val Leu Ala Glu Val Glu Ala Val Leu Ala Gly Val Glu Ala Glu Lys
                290                 295                 300

Leu Ala Gly Asn Ala Ser Trp Gly Glu Leu Phe Ser Ser Lys Thr Lys
305                 310                 315                 320

Val Leu Gln Arg Leu Ile Met Gly Ala Met Ile Gln Ser Leu Gln Gln
                325                 330                 335

Leu Thr Gly Asp Asn Tyr Phe Phe Tyr Tyr Gly Thr Thr Ile Phe Lys
                340                 345                 350

Ala Val Gly Leu Ser Asp Ser Phe Glu Thr Ser Ile Val Leu Gly Ile
                355                 360                 365

Val Asn Phe Ala Ser Thr Phe Val Gly Ile Tyr Val Val Glu Arg Tyr
                370                 375                 380

Gly Arg Arg Thr Cys Leu Leu Trp Gly Ala Ala Ser Met Thr Ala Cys
385                 390                 395                 400

Met Val Val Tyr Ala Ser Val Gly Val Thr Arg Leu Trp Pro Asn Gly
                405                 410                 415

Gln Asp Gln Pro Ser Ser Lys Gly Ala Gly Asn Cys Met Ile Val Phe
                420                 425                 430

Ala Cys Phe Tyr Ile Phe Cys Phe Ala Thr Thr Trp Ala Pro Ile Pro
                435                 440                 445

Tyr Val Val Val Ser Glu Thr Phe Pro Leu Arg Val Lys Ser Lys Ala
                450                 455                 460

Met Ser Ile Ala Thr Ala Ala Asn Trp Leu Trp Gly Phe Leu Ile Gly
465                 470                 475                 480
```

```
Phe Phe Thr Pro Phe Ile Thr Gly Ala Ile Asn Tyr Tyr Gly Tyr
                485                 490                 495

Val Phe Met Gly Cys Leu Val Phe Met Phe Tyr Val Leu Leu Val
            500                 505                 510

Val Pro Glu Thr Lys Gly Leu Thr Leu Glu Glu Val Asn Thr Met Trp
            515                 520                 525

Glu Glu Gly Val Leu Pro Trp Lys Ser Ala Ser Trp Val Pro Pro Ser
530                 535                 540

Arg Arg Gly Ala Asn Tyr Asp Ala Glu Glu Met Thr His Asp Asp Lys
545                 550                 555                 560

Pro Leu Tyr Lys Arg Met Phe Ser Thr Lys
                565                 570
```

<210> SEQ ID NO 2
<211> LENGTH: 570
<212> TYPE: PRT
<213> ORGANISM: Saccharomyces cerevisiae

<400> SEQUENCE: 2

```
Met Ser Gln Asp Ala Ala Ile Ala Glu Gln Thr Pro Val Glu His Leu
1               5                   10                  15

Ser Ala Val Asp Ser Ala Ser His Ser Val Leu Ser Thr Pro Ser Asn
                20                  25                  30

Lys Ala Glu Arg Asp Glu Ile Lys Ala Tyr Gly Glu Gly Glu His
            35                  40                  45

Glu Pro Val Val Glu Ile Pro Lys Arg Pro Ala Ser Ala Tyr Val Thr
50                  55                  60

Val Ser Ile Met Cys Ile Met Ile Ala Phe Gly Phe Val Ser Gly
65                  70                  75                  80

Trp Asp Thr Gly Thr Ile Ser Gly Phe Ile Asn Gln Thr Asp Phe Ile
                85                  90                  95

Arg Arg Phe Gly Met Lys His Lys Asp Gly Thr Asn Tyr Leu Ser Lys
            100                 105                 110

Val Arg Thr Gly Leu Ile Val Ser Ile Phe Asn Ile Gly Cys Ala Ile
            115                 120                 125

Gly Gly Ile Ile Leu Ser Lys Leu Gly Asp Met Tyr Gly Arg Lys Val
130                 135                 140

Gly Leu Ile Val Val Val Val Tyr Ile Ile Gly Ile Ile Gln
145                 150                 155                 160

Ile Ala Ser Ile Asn Lys Trp Tyr Gln Tyr Phe Ile Gly Arg Ile Ile
                165                 170                 175

Ser Gly Leu Gly Val Gly Gly Ile Ala Val Leu Ser Pro Met Leu Ile
            180                 185                 190

Ser Glu Val Ser Pro Lys His Leu Arg Gly Thr Leu Val Ser Cys Tyr
            195                 200                 205

Gln Leu Met Ile Thr Ala Gly Ile Phe Leu Gly Tyr Cys Thr Asn Phe
210                 215                 220

Gly Thr Lys Asn Tyr Ser Asn Ser Val Gln Trp Arg Val Pro Leu Gly
225                 230                 235                 240

Leu Cys Phe Ala Trp Ala Leu Phe Met Ile Gly Gly Met Thr Phe Val
                245                 250                 255

Pro Glu Ser Pro Arg Tyr Leu Ala Glu Val Gly Lys Ile Glu Glu Ala
            260                 265                 270

Lys Arg Ser Ile Ala Val Ser Asn Lys Val Ala Val Asp Asp Pro Ser
            275                 280                 285
```

```
Val Leu Ala Glu Val Glu Ala Val Leu Ala Gly Val Glu Ala Glu Lys
        290                 295                 300

Leu Ala Gly Asn Ala Ser Trp Gly Glu Leu Phe Ser Ser Lys Thr Lys
305                 310                 315                 320

Val Leu Gln Arg Leu Ile Met Gly Ala Met Ile Gln Ser Leu Gln Gln
                325                 330                 335

Leu Thr Gly Asp Asn Tyr Phe Phe Tyr Tyr Gly Thr Thr Ile Phe Lys
                340                 345                 350

Ala Val Gly Leu Ser Asp Ser Phe Glu Thr Ser Ile Val Leu Gly Ile
                355                 360                 365

Val Asn Phe Ala Ser Thr Phe Val Gly Ile Tyr Val Val Glu Arg Tyr
        370                 375                 380

Gly Arg Arg Thr Cys Leu Leu Trp Gly Ala Ala Ser Met Thr Ala Cys
385                 390                 395                 400

Met Val Val Tyr Ala Ser Val Gly Val Thr Arg Leu Trp Pro Asn Gly
                405                 410                 415

Gln Asp Gln Pro Ser Ser Lys Gly Ala Gly Asn Cys Met Ile Val Phe
                420                 425                 430

Ala Cys Phe Tyr Ile Phe Cys Phe Ala Thr Thr Trp Ala Pro Ile Pro
                435                 440                 445

Tyr Val Val Ser Glu Thr Phe Pro Leu Arg Val Lys Ser Lys Ala
        450                 455                 460

Met Ser Ile Ala Thr Ala Ala Asn Trp Leu Trp Gly Phe Leu Ile Gly
465                 470                 475                 480

Phe Phe Thr Pro Phe Ile Thr Gly Ala Ile Asn Phe Tyr Tyr Gly Tyr
                485                 490                 495

Val Phe Met Gly Cys Leu Val Phe Met Phe Tyr Val Leu Leu Val
                500                 505                 510

Val Pro Glu Thr Lys Gly Leu Thr Leu Glu Glu Val Asn Thr Met Trp
        515                 520                 525

Glu Glu Gly Val Leu Pro Trp Lys Ser Ala Ser Trp Val Pro Pro Ser
530                 535                 540

Arg Arg Gly Ala Asn Tyr Asp Ala Glu Glu Met Thr His Asp Asp Lys
545                 550                 555                 560

Pro Leu Tyr Lys Arg Met Phe Ser Thr Lys
                565                 570

<210> SEQ ID NO 3
<211> LENGTH: 1713
<212> TYPE: DNA
<213> ORGANISM: Saccharomyces cerevisiae

<400> SEQUENCE: 3
atgtcacaag acgctgctat tgcagagcaa actcctgtgg agcatctctc tgctgttgac      60
tcagcctccc actcggtttt atctacacca tcaaacaagg ctgaaagaga tgaaataaaa     120
gcttatggtg aaggtgaaga gcacgaacct gtcgttgaaa ttccaaagag accagcttct     180
gcctatgtca ctgtctctat tatgtgtatc atgatcgcct ttggtggttt cgttttcggt     240
tgggatactg gtaccatttc tggtttcatc aatcaaaccg atttcatcag aagatttggt     300
atgaagcata agatggtac taattatttg tctaaggtta gaactggttt gattgtctcc     360
attttcaaca ttggttgtgc cattggtggt attattcttt ccaaattggg tgatatgtac     420
ggtcgtaagg tgggtttgat tgtcgttgtt gtcatctaca tcatcggtat tattattcaa     480
```

```
attgcatcta tcaacaaatg gtaccaatat ttcatcggta gaattatttc cggtttgggt    540
gttggtggta ttgccgtttt atctcctatg ttgatttctg aagtatcccc aaagcattta    600
aggggtactt tagtctcttg ctaccaattg atgattactg ccggtatttt cttgggttac    660
tgtaccaact tcggtactaa gaactactcc aactctgtgc aatggagagt tccattaggt    720
ttgtgttttg cctgggcttt gtttatgatt ggtggtatga catttgttcc agagtctcca    780
cgttatttgg ctgaagtcgg taagatcgaa gaagccaaac gttctattgc cgtttctaac    840
aaggttgctg ttgatgatcc atctgttttg gctgaagtcg aagctgtctt ggctggtgta    900
gaggcagaga aattagctgg taatgcatcc tggggtgaat tgtttagtag caagacaaag    960
gtccttcagc gtttgatcat gggtgctatg attcaatctc tacaacaatt gacaggtgat   1020
aactatttct tctactatgg tactactatt ttcaaggctg ttggtttgag tgactctttc   1080
gaaacctcta ttgtcttggg tattgttaac tttgcttcca cctttgttgg tatttacgtt   1140
gttgagagat atggtcgtcg tacttgtttt ctatggggtg ctgcatccat gactgcttgt   1200
atggttgtct atgcttccgt gggtgtcacc agattatggc caaatggtca agaccaacca   1260
tcttccaagg gtgctggtaa ctgtatgatt gtctttgcct gtttctatat tttctgtttt   1320
gctactacat gggctccaat tccttatgtc gttgtttctg aaactttccc attgagagtc   1380
aagtctaagg ctatgtctat tgctacagct gctaattggt tgtggggttt cttgattggt   1440
ttcttcactc catttattac tggtgctatt aacttctact acggttacgt tttcatgggc   1500
tgtttggtct tcatgttctt ctatgttttg ttagttgttc agaaactaa gggtttgact    1560
ttggaagaag tcaacaccat gtgggaagaa ggtgttctac catggaagtc tgcctcatgg   1620
gttccaccat ccagaagagg tgccaactac gacgctgaag aaatgactca cgatgacaag   1680
ccattgtaca agagaatgtt cagcaccaaa taa                                 1713

<210> SEQ ID NO 4
<211> LENGTH: 1713
<212> TYPE: DNA
<213> ORGANISM: Saccharomyces cerevisiae

<400> SEQUENCE: 4
atgtcacaag acgctgctat tgcagagcaa actcctgtgg agcatctctc tgctgttgac     60
tcagcctccc actcggtttt atctacacca tcaaacaagg ctgaaagaga tgaaataaaa    120
gcttatggtg aaggtgaaga gcacgaacct gtcgttgaaa ttccaaagag accagcttct    180
gcctatgtca ctgtctctat tatgtgtatc atgatcgcct ttggtggttt cgtttccggt    240
tgggatactg gtaccatttc tggtttcatc aatcaaaccg atttcatcag aagatttggt    300
atgaagcata agatggtac taattatttg tctaaggtta aactggtttt gattgtctcc    360
attttcaaca ttggttgtgc cattggtggt attattcttt ccaaattggg tgatatgtac    420
ggtcgtaagg tgggtttgat tgtcgttgtt gtcatctaca tcatcggtat tattattcaa    480
attgcatcta tcaacaaatg gtaccaatat ttcatcggta gaattatttc cggtttgggt    540
gttggtggta ttgccgtttt atctcctatg ttgatttctg aagtatcccc aaagcattta    600
aggggtactt tagtctcttg ctaccaattg atgattactg ccggtatttt cttgggttac    660
tgtaccaact tcggtactaa gaactactcc aactctgtgc aatggagagt tccattaggt    720
ttgtgttttg cctgggcttt gtttatgatt ggtggtatga catttgttcc agagtctcca    780
cgttatttgg ctgaagtcgg taagatcgaa gaagccaaac gttctattgc cgtttctaac    840
aaggttgctg ttgatgatcc atctgttttg gctgaagtcg aagctgtctt ggctggtgta    900
```

```
gaggcagaga aattagctgg taatgcatcc tggggtgaat tgtttagtag caagacaaag    960
gtccttcagc gtttgatcat gggtgctatg attcaatctc tacaacaatt gacaggtgat   1020
aactatttct tctactatgg tactactatt ttcaaggctg ttggtttgag tgactctttc   1080
gaaacctcta ttgtcttggg tattgttaac tttgcttcca cctttgttgg tatttacgtt   1140
gttgagagat atggtcgtcg tacttgtttg ctatggggtg ctgcatccat gactgcttgt   1200
atggttgtct atgcttccgt gggtgtcacc agattatggc caaatggtca agaccaacca   1260
tcttccaagg gtgctggtaa ctgtatgatt gtctttgcct gtttctatat tttctgtttt   1320
gctactacat gggctccaat tcctatgtc gttgtttctg aaactttccc attgagagtc   1380
aagtctaagg ctatgtctat tgctacagct gctaattggt tgtggggttt cttgattggt   1440
ttcttcactc catttattac tggtgctatt aacttctact acggttacgt tttcatgggc   1500
tgtttggtct tcatgttctt ctatgttttg ttagttgttc cagaaactaa gggtttgact   1560
ttggaagaag tcaacaccat gtgggaagaa ggtgttctac catggaagtc tgcctcatgg   1620
gttccaccat ccagaagagg tgccaactac gacgctgaag aaatgactca cgatgacaag   1680
ccattgtaca agagaatgtt cagcaccaaa taa                                1713
```